United States Patent [19]

Zaffaroni et al.

[11] 4,096,238

[45] Jun. 20, 1978

[54] METHOD FOR ADMINISTERING DRUG TO THE GASTROINTESTINAL TRACT

[75] Inventors: Alejandro Zaffaroni; Alan S. Michaels, both of Atherton; Felix Theeuwes, Los Altos, all of Calif.

[73] Assignee: Alza Corporation, Palo Alto, Calif.

[21] Appl. No.: 775,774

[22] Filed: Mar. 9, 1977

Related U.S. Application Data

[60] Division of Ser. No. 536,006, Dec. 23, 1974, Pat. No. 4,036,227, which is a continuation-in-part of Ser. No. 354,344, Apr. 25, 1973, abandoned.

[51] Int. Cl.$^2$ ................................................ A61K 9/22
[52] U.S. Cl. ...................................... 424/15; 128/260
[58] Field of Search ..................... 128/260; 424/14–22

[56] References Cited

U.S. PATENT DOCUMENTS

| 216,107 | 6/1879 | Richards | 424/15 |
|---|---|---|---|
| 3,113,076 | 12/1963 | Jacobs | 424/15 X |
| 3,146,169 | 8/1964 | Stephenson et al. | 424/15 |
| 3,845,770 | 11/1974 | Theeuwes et al. | 128/260 |
| 3,916,899 | 11/1975 | Theeuwes et al. | 128/260 |
| 4,036,227 | 7/1977 | Zaffaroni et al. | 128/260 |

Primary Examiner—Shep K. Rose
Attorney, Agent, or Firm—Paul L. Sabatine; Thomas E. Ciotti; Edward L. Mandell

[57] ABSTRACT

An osmotic device for releasing a useful agent at different release rate patterns from the device in a selected environment is disclosed. The device is comprised of a wall surrounding and forming a compartment as a means for containing a useful agent and having a passageway for releasing the agent. The wall is comprised in at least a part of a material permeable to an external fluid and impermeable to the agent. A layer of a pattern rate controlling material that erodes in a selected environment for changing the release rate pattern of the device is carried on the semipermeable wall distant from the compartment. The agent is soluble in the fluid and exhibits an osmotic pressure gradient across the semipermeable wall against the fluid or the agent has limited solubility and is admixed with an osmotically effective solute soluble in the fluid that exhibits an osmotic pressure gradient across the semipermeable wall against the fluid. In operation, agent is released from the device at different release rate patterns by the pattern rate controlling material eroding at a controlled rate to increase the amount of fluid available to the semipermeable wall for imbibition, which fluid is imbibed through the wall into the compartment producing a solution of the soluble agent or a solution of the osmotically effective solute containing the agent which is released through the passageway to the exterior of the device at a rate controlled by the permeability of the semipermeable wall and the osmotic pressure gradient across the wall of the device.

1 Claim, 18 Drawing Figures

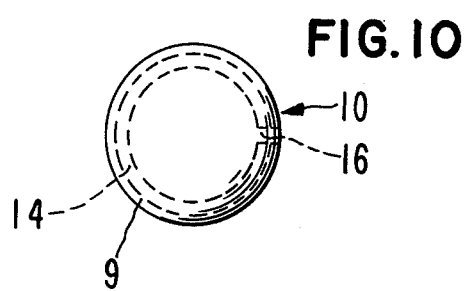
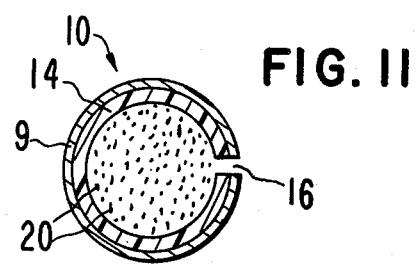
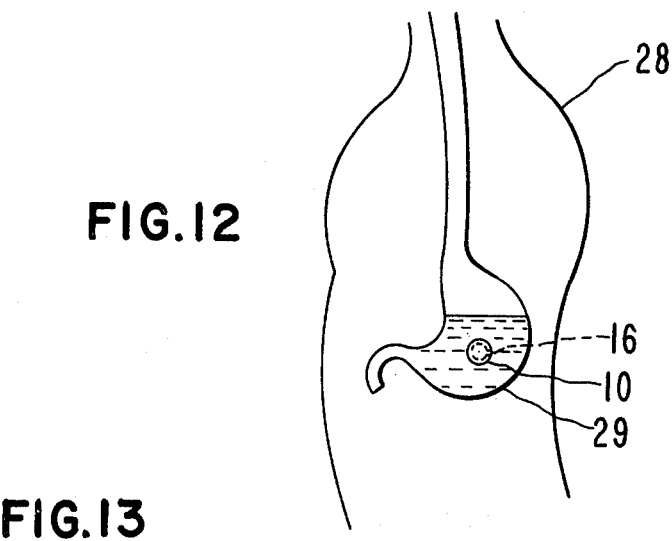
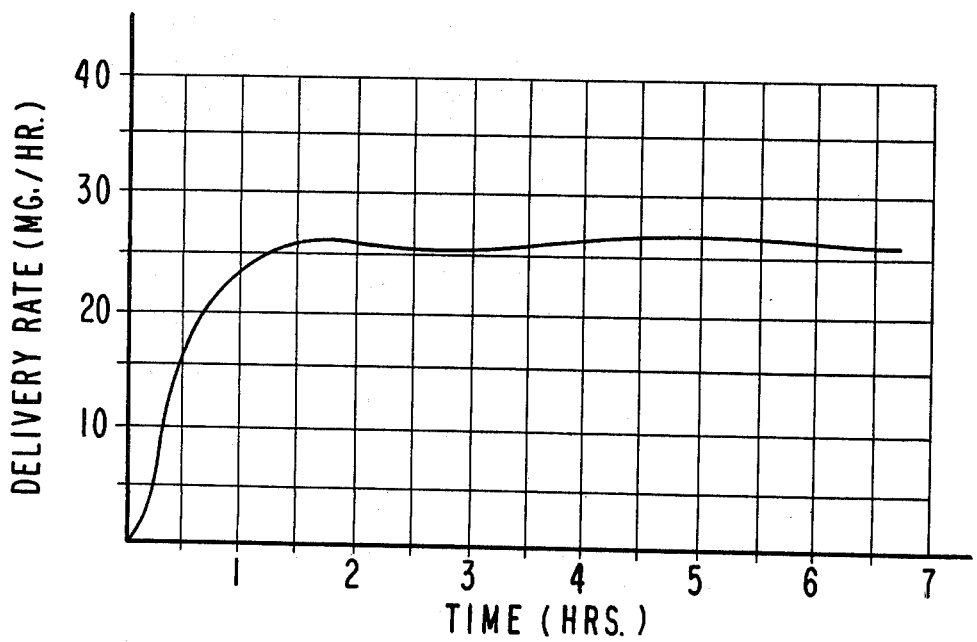

METHOD FOR ADMINISTERING DRUG TO THE GASTROINTESTINAL TRACT

CROSS-REFERENCE TO RELATED APPLICATIONS

This application is a division of U.S. patent application Ser. No. 536,006 filed on Dec. 23, 1974, now U.S. Pat. No. 4,036,227, which application is a continuation-in-part of U.S. patent application Ser. No. 354,344 filed Apr. 25, 1973, now abandoned. These applications are assigned to the ALZA Corporation, 950 Page Mill Road, Palo Alto, California, 94304, which applications are incorporated herein, and benefit of their filing dates is claimed.

FIELD OF THE INVENTION

This invention pertains to both a novel and useful osmotic device for releasing a useful agent. More particularly, the invention relates to an osmotic device having a means for changing its release rate pattern for the subsequent release of the agent at a controlled and continuous rate over a prolonged period of time to produce a beneficial effect. Specifically, the invention concerns an osmotic dispenser manufactured with a minimum number of components, suitable for administering an active agent and having a means for regulating the amount of agent released at preselected patterns at a controlled and continuous rate to achieve a predetermined useful effect in animals, humans and other environments.

BACKGROUND OF THE INVENTION

Dispensing systems for the delivery of useful agents are well known to the prior art. These systems generally deliver their agent by diffusion, for example, from an enclosed capsule or by diffusion from a multi-structured device having a wall formed of a known polymer permeable to the agent into a selected environment. However, there is a large category of agents that cannot be delivered by the prior art delivery systems because of at least one feature inherent in those devices which adversely affects their rate of release from the system or substantially prevents the release of the agent from the system. For example, many agents cannot be delivered from a diffusion controlled delivery system because their permeation rate through the rate controlling material comprising the system is too small to produce a useful effect or in many instances the agent molecules are too big and will not diffuse through the rate controlling material forming the device. Also, there is an additional class of useful agents that cannot be satisfactorily delivered by diffusion devices because of a particular chemical characteristic of the agent. This additional class includes salts that because of their ionic character will not diffuse through most polymers and polymeric like materials and unstable polar compounds that cannot be formulated into a satisfactory composition suitable for storage and delivery from a prior art device. Prior art diffusion systems encompassed within the above discussion are typically represented by U.S. Pat. No. 3,279,996, and the like.

The prior art attempted to overcome the above mentioned adverse features by proposing devices seemingly capable of releasing a solution containing a product at a relatively constant rate. One such device is disclosed in *Austral. J. Exp. Biol.*, Vol. 33, pages 415 to 420, 1955. This device consists of three compartments confined in a specially constructed housing and a clamp to hold a semi-permeable membrane. The driving force of the device depends on the continual presence of a solution of an osmotically effective red dye solute that exhibits an osmotic pressure gradient against water. The red dye is contained in a partially collapsed rubber compartment and it is separated from a second compartment containing water by a semi-permeable membrane. The partially collapsed bag is housed in a glass ampoule, along with a product compartment defined by the space between the bag and one end of the glass ampoule. The distant end of the ampoule defines a water compartment. The ampoule also is provided with a drug release nipple, and in operation when the product compartment is charged with a solution of a product, water in the water compartment moves through the semi-permeable membrane into the dye solution increasing its volume in the compartment causing it to expand against the rubber providing the mechanical force necessary to eject the product solution through the nipple. It is immediately evident that this device has certain adverse features that tend to diminish its practical use. For example, the device is difficult to construct into compartments that are essentially free of leaks plus the fabrication demands of a movable material that necessitates a rigid outer housing. Another inherent disadvantage which prevented its wide acceptance by the medical community is the requirement that the product be in solution which exhibit a deleterious tendency to be released from the device by simple leaching, the use of a solution of the product which use does not permit high concentrations of the product to be embodied within the device, the demand for an osmotically effective solute other than the product, and that many products on prolonged storage in solution undergo chemical deterioration. The device is further of limited value because it must carry its own water which increases the size of the device and thusly limits its use to a few environments. Another prior art attempt to provide a product dispensing device is disclosed in U.S. Pat. No. 3,604,417. The device disclosed in this patent is similar to the earlier prior art devices, and its design requires a semi-permeable membrane, a separate osmotically effective solute, a solution of the product and additionally the presence of a movable piston. The movable piston severely restricts the shape of the device, and this device, as with the above mentioned device, has not enjoyed wide acceptance because of construction problems and the inherent features that limit the use of the deivce.

In prior art U.S. Pat. No. 3,146,169 there is disclosed a pharmaceutical tablet formulation comprised of a layer impermeable to both water and medication which surrounds the medication except for a hole. In this device medication is released by uncontrolled dissolution predicated upon many variables. For example, the rate of medication dissolution is pH dependent that varies according to the environment, and when it changes the solubility of the medication its rate of release is correspondingly changed. The rate of release is also stirring rate dependent and any external fluid must be in a constant state of flux to cause a dissolution of the product for its release from the tablet. Hence, if there is little or no external fluid, the product will not be released from the device. Further, in this tablet the exposed surface area of the product continually changes at an uncontrolled rate to release product in changing amounts, which features seriously limit the usefulness of the tablet. Also, as the exposed surface area of medication and the length of the diffusional path change, the amount of medication released becomes unpredictable and, as such, this device cannot be relied upon for use in the management of health and disease.

Other prior art attempts to provide a controlled dosage release is described in U.S. Pat. No. 3,247,066. In this patent a device is described comprised of a polymeric wall that fully surrounds a drug colloid mixture. Drug is released from the device under the influence of water entering the mixture to cause an increased internal swelling pressure of the colloid that builds up sufficiently to exceed the strength of the polymer wall. The build-up is followed by a rupture of the wall that immediately releases drug in an undetermined amount. This action, plus any subsequent drug release, is by seemingly uncontrolled dissolution which features tend to inherently limit the acceptability of this device for the controlled and prolonged administration of drug. Similarly, in U.S. Pat. No. 3,538,214 there is disclosed a tablet comprised of a drug matrix coated with a microporous film permeable to fluid and drug as another prior art means for the controlled release of drug. The device of this patent releases drug by letting water pass through the pores to dissolve drug which is released through the pores. The rate of drug release is again influenced by environmental factors such as pH dependency and this coupled with both an unspecified number of pores of variable sizes arising through manufacture and material limitations limits the use of this device in the useful arts and sciences.

In copending patent application U.S. Ser. No. 259,469, filed on June 5, 1973, now U.S. Pat. No. 3,845,770 and U.S. patent application Ser. No. 440,281, filed on Feb. 7, 1974, which applications are assigned to the same assignee of this patentable invention, there are disclosed novel and useful dispenser devices that represent both a pioneer contribution and improvement to the dispensing art. While the devices of that invention give outstanding, operable and useful results and release their agent at an osmotically controlled rate, it has now been found that a unique means for letting the device release their agent only in certain environments or for changing the release rate pattern of the agent can be manufactured into the device. It will be appreciated by those versed in the art to which the invention pertains that this means not only increases the usefulness of the device but enhances its range of operation as a useful article of manufacture.

OBJECTS OF THE INVENTION

Accordingly, it is an immediate object of this invention to provide a novel dispensing device for the dispensing of a useful agent to product a beneficial effect, which device overcomes the aforesaid disadvantages associated with the prior art devices.

Another object of the invention is to provide a new and useful delivery device for the administration of an active agent wherein the device is nonrupturable and maintains its physical and chemical integrity throughout its agent-release history.

Yet another object of the invention is to provide a new and useful delivery device for the controlled and uniform release of an active agent wherein the agent is released from the device in a selected environment at a rate controlled by the device.

Still another object of the invention is to provide an osmotic agent delivery device for the prolonged essentially zero order release of agent wherein agent is released independently of pH.

Yet still a further object of the invention is to provide a novel and useful osmotic drug delivery device that releases active agent essentially free of any stirring rate dependency at a constant and controlled rate over a prolonged time.

Yet still a further object of the invention is to provide a novel and useful drug delivery device wherein the drug is essentially released by osmotic action and the device is adapted for animal, including humans, animal orifices and passageways, or for implantation into animal, including human, bodies.

Still a further object of the invention is to provide an osmotic delivery device for osmotically dispensing an active agent into fields, rivers, streams and the like.

Still another object of the invention is to provide a novel dispensing device for dispensing a composition of matter at a controlled rate for a prolonged period of time.

Yet still another object of this invention is to provide a device that is simple in construction, designed with a minimum number of parts, easy to use, and in operation exhibits all the practical and useful benefits obtained by the controlled, continuous, long-term administration of various compositions of matter, that is, active agents to animals, avians, humans and into other environments.

Yet another object of the invention is to provide a device containing agent surrounded with a coated semipermeable membrane except for a passageway through which drug is released. In use, the exterior coat erodes to expose the semipermeable membrane for the osmotically controlled release of agent for a prolonged period of time from the device.

A further object of this invention is to provide a device containing agent surrounded with a coated semipermeable membrane except for a passageway through which drug is released. In use, the exterior coat erodes to increase the amount of fluid available to the wall for imbibition which is imbibed into the compartment for osmotically controlled release of agent.

Another object of this invention is to provide an improved dispensing device which will permit high concentration of an active agent to be contained therein, and which high concentration of the agent will not exhibit the tendency to be leached from the device nor have its potency decreased by chemical breakdowns.

Yet still a further object of the invention is to provide a novel product dispensing device that contains a useful agent which agent can also be used as an osmotically effective solute to exhibit an osmotic pressure gradient against an external fluid.

Yet a further object of the invention is to provide an agent dispensing device that contains an agent in a form suitable for storage thereby giving the device an improved shelf life.

Yet another immediate object of this invention is to provide a dispensing device for the administration of locally acting or systemically acting drugs to produce a physiologic or pharmacologic effect and which device can release the drug in preselected biological environment, at different release patterns and at a rate that does not vary with time.

Still yet another object of the invention is to provide a device bearing an exterior layer on a semipermeable membrane and containing drugs in various physicochemical forms that can be sterilized when needed by operable conventional techniques.

Yet another object is to provide a device for dispensing an agent which device can have a variety of release rates ranging from low to very high by using polymeric wall forming materials in combination with a semipermeable membrane and wherein the polymeric wall material controllably erodes to correspondingly expose or increase the amount of fluid available to the semipermeable membrane for subsequent release of agent from the device.

Yet still another object of the invention is to provide a novel and useful erodible or biodegradable device that erodes or degrades after the device has released the active agent, or at the end of the drug release rate preprogrammed history.

Yet still a further object of the invention is to provide an osmotic device having a means for letting the device release in certain environments of use, or for letting the device incrementally change the amount of agent to be subsequently released at a continuous and controlled rate over a prolonged period of time.

Other objects, features, and advantages of the invention will be apparent to those skilled in the art from the detailed description of this specification, taken in conjunction with the drawings and the accompanying claims.

SUMMARY OF THE INVENTION

The invention concerns a device comprised of a wall surrounding a compartment as a means for containing a useful agent, such as a composition of matter, a drug, a beneficial product or the like, and having a passageway communicating with the compartment and the exterior of the device for releasing the agent, or the like, from the compartment. The wall of the device is comprised in at least a part of a material that is semipermeable to external fluid common to the environment of use and essentially impermeable to the useful agent or the like. A layer or coat of an erodible material that erodes in certain environments is carried exteriorly on the semipermeable wall. Agent is released from the device by the coat eroding to let the external fluid permeate through the wall into the compartment to dissolve the agent or to dissolve an osmotically effective compound admixed with agent having limited solubility in the fluid in the compartment, producing thereby an essentially saturated solution of the agent or an essentially saturated solution of the osmotic compound containing the latter agent, which solution in either instance is released from the device by a constant influx of fluid from the environment and wherein the influx is generated by the continuous internal dissolution of the agent or the osmotically effective compound in the fluid diffusing at a controlled rate through the wall under the osmotic pressure gradient across the wall into the compartment. The device can in operation dispense agent at a zero order rate of release for a prolonged period of time by maintaining the rate of internal dissolution of the agent, or the osmotic compound in the fluid constant. In the device the latter is accomplished when the dissolution rate is larger than the rate of release of the agent or the osmotic compound in the fluid in the device. This fluid enters the device as the outside coating erodes, and fluid leaves the device at a rate controlled by the permeability of the semipermeable wall and the osmotic pressure gradient across the semipermeable wall of the device.

BRIEF DESCRIPTION OF THE DRAWINGS

In the drawings, which are not drawn to scale, but rather are set forth to illustrate various embodiments of the invention, there appears as follows:

FIG. 10 illustrates an oral osmotic drug delivery tablet for osmotically administering a physiologically or pharmacologically-effective amount in the gastro-intestinal tract of animals including veterinary animals and humans.

FIG. 11 is a cross-sectional of the device of FIG. 9 with the top portioned section to lay open the interior structure of the osmotic oral dosage form of FIG. 9.

FIG. 12 is a view diagrammatically illustrating an osmotic drug delivery device manufactured according to the invention in an environment of use, such as the stomach.

FIG. 13 is a graph showing a controlled and constant rate of release for the device over a prolonged period of time.

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
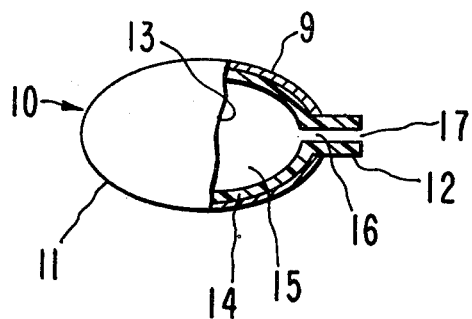
FIG. 1 is an illustration of a delivery device of the invention with a portion of the wall removed to illustrate the general structure of the device comprised of an exterior coat on a semipermeable wall.

Turning now to the drawings in detail, which are examples of various delivery devices of the invention, and which examples are not to be construed as limiting, one embodiment of a novel osmotic delivery device is indicated in FIG. 1 by the number 10. Delivery device 10 is comprised of a body portion 11 and a neck 12 suitably joined to body 11. Device 10 is shown in open section 13 with part of a wall removed and device 10 is comprised of a wall 14 surrounding a compartment 15. Compartment 15 is a means for containing an agent, that is, it is a product compartment, and it can contain a product, or a mixture of products such as a drug or other useful active agent, not shown in FIG. 1. Neck 12 of device 10 in this embodiment is extended from body 11 and it is formed with a passageway 16 that communicates with chamber 15 and the exterior of the device through opening 17 at the end of neck 12. Neck 12 can be optionally integrally formed with body 11, or it can be separately manufactured and then joined to body 11 by conventional techniques such as adhesively sealing, heat joining, laser sealing, and the like.

Wall 14 of delivery device 10 is comprised in total or in at least a part of a film forming semipermeable membrane that possesses permeability to an external fluid while simultaneously being essentially impermeable to a product in compartment 15. A layer or coat 9 is carried on at least a part or on all of semipermeable wall 14 distant from compartment 15. Layer 9 is made from a material that erodes or disintegrates to controllably make available fluid to semipermeable wall 14. That is, coating is a pattern rate controlling material and by controlling the amount of fluid available to the surface of wall 14, it operates to govern the amount of fluid present for imbibition by device 10. In another embodiment, layer 9 is made of a permeable material having a permeability p and a diffusional path or thickness $t$ to let the initial amount of fluid reach wall 14, and erodes to form decreasing thinner layers $t'$, $t''$ etc. thereby regulating and increasing the amount of fluid available for imbibition by device 10. In device 10, body 11 formed of wall 14 can be of unit construction, or composite construction with a section of semipermeable membrane either formed integral in wall 14, or optionally lined or laminated to wall 14. Wall 14 is formed of a semipermeable material that has uniform properties across all its dimensions, that is, it is substantially imperforate or substantially homogeneous while remaining essentially impermeable to a product present in compartment 15. Coat 9 can be a material that erodes at a controlled rate over a prolonged period of time in response to an essentially constant pH environment or in another embodiment it can be a material that erodes quickly at any given pH in the environment. In operation, coat 9 is impermeable to fluid and it quickly erodes to expose the semipermeable membrane 14 or it is impermeable and erodes at a controlled rate to continuously expose semipermeable wall 14. In another operation, coat 9 is permeable to fluid and it erodes from the exterior inwards, thereby increasing the amount of fluid available to wall 14. After wall 14 is contacted by fluids, molecules of the fluid dissolve in and diffuse through wall 14 by the process of osmotic diffusion into compartment 15. When wall 14 is formed in at least a part of a selectively permeable material or membrane permeable to the passage of an external fluid but impermeable to the passage of active agent, the remaining part of wall 14 is formed of a material that is substantially impermeable to the passage of external fluid and impermeable to the passage of active agent. Wall 14 is formed totally of synthetic or naturally occurring semipermeable materials or it can be formed in part of synthetic or naturally occurring semipermeable materials and in part of a synthetic or naturally occurring impermeable material. Coating 9 is formed totally of synthetic or naturally occurring materials and it can be formed in part of synthetic or naturally occurring materials, which material possess quick or slow erosion properties and is impermeable or permeable to the passage of external fluids. A detailed description of these materials appears later in this specification. The device of FIG. 1 can be adapted for releasing fertilizers in plowed fields, for releasing insecticides in streams, for releasing medications in farm animals including cattle, horses, sheep, pigs and the like, for releasing active agent in humans, such as in the eye, vagina or the like and other like uses.

Figure 2:
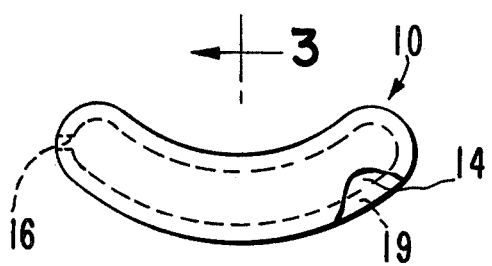
FIG. 2 is a perspective, top view of an ocular dispensing device of the invention illustrating as one embodiment of the invention a device manufactured, in this embodiment, as an ocular drug delivery device.

In FIG. 2 there is seen another delivery device 10 manufactured according to the mode and manner of the invention. Product delivery device 10 in this embodiment is an ocular drug delivery device of bean shape and it is illustrated in FIG. 2 in top perspective view. Ocular device 10 comprised of a wall 14 formed of a selectively permeable material that is permeable to an external fluid but substantially impermeable to active agent, drug and the like, not seen in FIG. 2 that is housed in device 10. Wall 14 is coated with a hydrophobic or a hydrophilic material not seen in FIG. 2, in whole or in part with a material that bioerodes in the environment of the eye over a prolonged period of time to expose wall 14 or let eye fluid diffuse therethrough to wall 14 at a rate corresponding to the erosion rate of the coating thereon. Device 10's outer wall 14 carries on its inner surface an inner positioned wall 19 formed with a passageway 16, schematically illustrated by dashed lines, which wall 19 is extended around the perimeter of wall 14 to engage it in sealed releation with another wall, not shown in FIG. 2 and positioned distant from illustrated wall 14. The distant wall can be of the same construction as wall 14, that is, a semipermeable material that may optionally bear an exterior hydrophobic coat thereon, or it can be formed of a material that is impermeable to an external fluid and impermeable to active agent and the like drug, to form device 10. Wall 14 of device 10 can be made of a material that is in part semipermeable and in part impermeable and these materials can be of synthetic or naturally occurring origin. Coat 9 is of like construction, that is of synthetic or naturally occurring origin.

Figure 3:
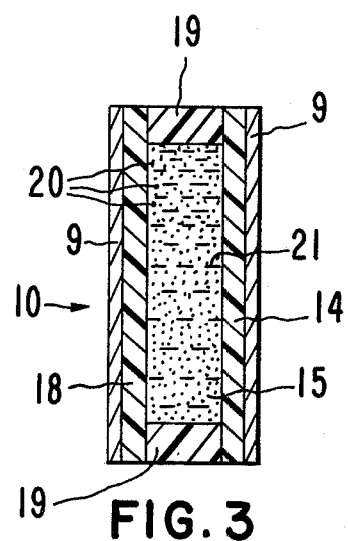
FIG. 3 is an enlarged cross-sectional view of the ocular drug delivery device of FIG. 2 through 3—3 depicting an exterior coat on a wall distant from a like structure with their interior peripheral surfaces in intimate contact with the surfaces of a wall positioned between the two walls.

Referring to FIG. 3, ocular drug delivery device 10 is seen in cross-section through 3—3 of FIG. 2. Ocular drug delivery device 10 of FIG. 3 is comprised of a first wall 14 and a third wall 18 distant from first wall 14. Wall 14 and wall 18 bear on their inner surface a second wall 19 that extends around the outer perimeter of wall 14 and wall 18 to form a closed drug compartment 15. Wall 14 and wall 18 bear on their outer surface a coating 9 of a release rate profile material, and this material on wall 14 and wall 18 may be of like or unlike chemical composition. Compartment 15 is comprised of a composition that is drug 20 or a mixture of drugs or the like. A passageway, not seen in FIG. 3, communicates with drug chamber 15 and the exterior of the device 10 for the release of drug 20. Wall 14 and wall 18 can be the same or they can be different and at least one of the walls, 14 or 18, or both of the walls, is comprised of a semi-permeable material selectively permeable to the passage of external fluid 21, for example, tear fluid in the eye as by diffusion, and substantially impermeable to active agent such as drug. While at least one of wall 14 or wall 18 is permeable to tear fluid 21, both of the walls are impermeable to the passage of drug 20. When wall 14 or wall 18 is formed of a semi-permeable membrane impermeable to drug, and the distant wall is formed of a different material, the latter material is substantially impermeable to both fluid and drug. In both structures the wall forming materals are substantially insoluble in body fluids and endowed with biological inertness. When at least one of wall 14 or 18 is coated 9, it is formed of a bioerodible release rate profile material such as a hydrophobic poly(carboxylic acid) having on the average one ionizable carboxylic hydrogen for each 8 to 22 total carbon atom, the distant wall may be coating-free, coated with a non-erodible material impermeable to tear fluid, or coated with a like material as the distant coating. Typical pharmaceutically acceptable coatings are disclosed later in the specification.

Wall 19 of device 10 of FIG. 3 is formed of a non-allergenic, biologically inert, insoluble in tear fluid material suitable for joining wall 14 and wall 18 together to form an essentially closed compartment 15 as defined by the inner surfaces of walls 14, 18 and 19. Device 10 when made from a material that is insoluble in tear fluid is removed from the eye after it completes its drug release program and discarded, or, device 10 can be made from a semipermeable bioerodible material that timely bioerodes in situ to harmless end products only after the device has completed its predetermined drug release program to the eye. The walls 14, 18 and 19 of device 10 fo the invention are formed of a material that can be rigid, semi-rigid, semi-flexible, flexible or the like and for the user's comfort in contact with skin, in body cavities, or in the eye it is preferably a flexible material that retains its physicochemical integrity throughout the drug release history.

Figure 4:
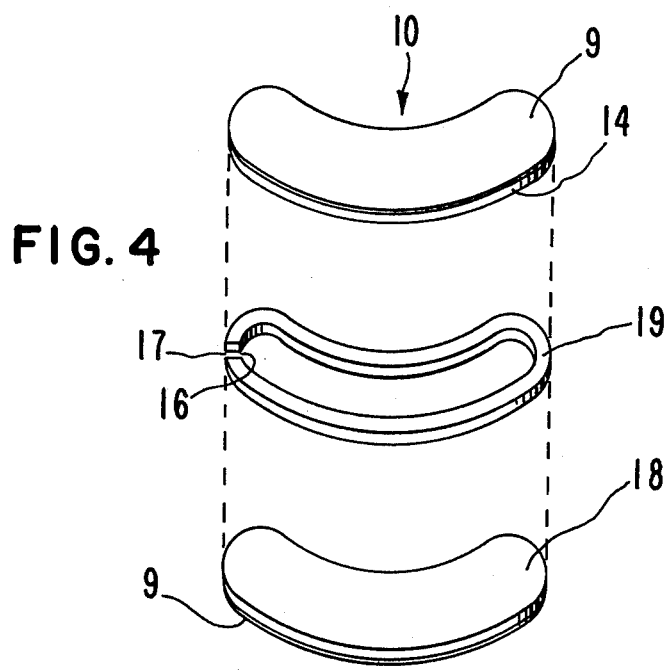
FIG. 4 is an exploded view illustrating three walls with at least one distant wall carrying a coating prior to their union wherein they act in concert to form a novel ocular drug delivery device.

In FIG. 4 there is illustrated the ocular drug delivery device 10 of FIGS. 2 and 3 in expanded view just prior to the joining of the parts into a composite article of manufacture. In device 10, the parts act in concert as an ocular drug delivery device to effectively meter a drug to the eye and to its surrounding tissues at a controlled and continuous osmotic rate for a prolonged period of time for the management of health and disease. Ocular drug delivery device 10 is comprised of a wall 14, a distant wall 18 and an inner wall for sealingly joining the inner perimeter of wall 14 to wall 19 and wall 18 to wall 14 into sealed relation to form a drug compartment defined by the inner surface of the walls for containing a drug not shown in FIG. 4. Wall 14 and/or wall 18 carry on their outer surface a hydrophobic, bioerodible layer 9 that erodes at a controlled rate over a prolonged period of time in response to the environment of the eye to change or regulate at a corresponding controlled rate the release rate profile of the ocular drug delivery device. Wall 19 has a passageway 16 that extends through wall 19 and ends at orifice 17 to permit the passage of a drug from the compartment to the exterior of the device. Ocular drug device 10 can also have passageway 16 through wall 14 or wall 18 in lieu of the passageway through wall 19. Also, the device can be constructed with one or more passageways that are the functional equivalent in an operative embodiment of a single passageway. Passageway 16 can be of any geometri shape, for example, round, triangular, square, elliptical, and the like. Drug 20 not shown in FIG. 4, as contained in device 10 is in solid form, as a tablet, film, in films mixed with a binder, granules, powdered, a solid suspension, particles in liquid, liquid emulsions containing solids, solids in solids and the like, and it can be geometric pieces of different shapes such as square, oval, round and rectangular. Drug 20 is soluble in tear fluid, which is substantially an aqueous medium, that is water, and product 20 exhibits an osmotic pressure gradient across exposed semipermeable membrane against external tear fluid 21. The osmotic pressure gradient generally is dependent on the solubility of the product or solute in the fluid and the concentration difference across the wall. This osmotic pressure gradient between drug in the compartment and the external fluid will cause water to permeate through the wall into the compartment of the drug and creating a hydrostatic pressure difference between the inside and the outside of the device. In operation, the release rate profile for the release of drug 20 from the device is first determined by the erodible layer 9 eroding to expose the wall surface, or to regulate the amount of fluid available to wall 14 for imbibition, and then drug is released through passageway 16 by external fluid being imbibed through semipermeable walls 14 or 18 or both into compartment 15 producing a solution of the drug which is released from the device at a rate corresponding to the rate controlled by the permeability of the semipermeable membrane to the fluid and the osmotic pressure gradient across the semipermeable wall between the drug in the compartment and the exterior fluid which combine to force drug solution from the device.

Figure 5:
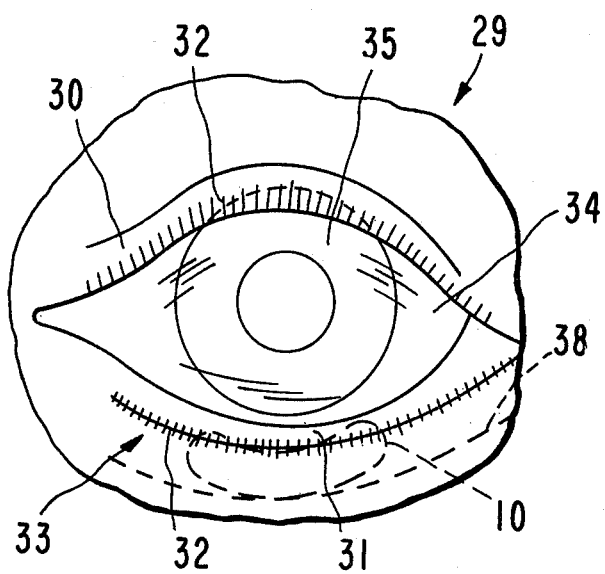
FIG. 5 is a partly diagrammatic, front view of a human eye illustrating an ocular drug delivery device of this invention in an operative position after its insertion into the eye.

Referring to FIG. 5 there is diagrammatically illustrated an ocular drug delivery device 10 positioned in immediate contact with an eyeball 29 for osmotically administering a beneficial drug to eye 29 at an osmotically metered dosage rate. In FIG. 5, eye 29 is comprised of an upper eyelid 30 and lower eyelid 31 with eyelashes 32 at the edge of eyelids 30 and 31. Eye 29 is comprised of an eyeball 33 covered for the greater part of its posterior area by sclera 34 and at its central area by a cornea 35. Eyelids 30 and 31 are lined with an epithelial membrane or palpebral conjunctiva, not shown, and sclera 34 is lined with a bulbar conjunctiva which covers the exposed surface of eyeball 33. Cornea 35 is covered with a transparent epithelial membrane, not shown in this figure. The portion of the palpebral conjunctiva which lines upper eyelid 30 and the underlying portion of the bulbar conjunctiva defines an upper cul-de-sac, not seen in FIG. 5, while that portion of the palpebral conjunctiva which lines lower eyelid 31 and the underlying portion of the bulbar conjunctiva defines a lower cul-de-sac, also not seen in FIG. 5. The osmotic drug delivery device 10 of this invention is designed for insertion in the cul-de-sac of the conjunctiva between sclera 34 of eyeball 33 and upper eyelid 30, or device 10 as seen in broken continuous lines is adapted for positioning in the cul-de-sac of the conjunctiva between the sclera 34 of eyeball 33 and lower eyelid 31, generally to be held in drug administration position by the natural pressure of the respective eyelid.

Figure 6:
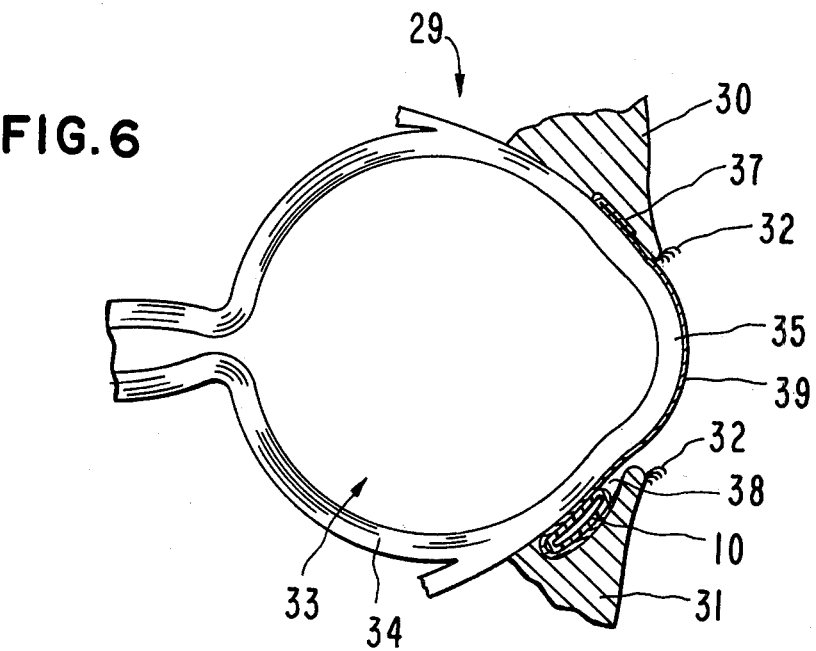
FIG. 6 is a view partly invertical section and partly diagrammatic of an eyeball and the upper and lower eyelids associated therewith showing the novel ocular product dispensing device of this invention in product administration operative position.

Turning to FIG. 6, which is considered in cooperation with FIG. 5, there is seen a horizontal section through a hyman eye 29 illustrating an osmotic ocular drug delivery device 10 in drug administration position. Eye 29 is generically comprised of upper eyelid 30 and lower eyelid 31 with their respective eyelashes 32. Eye 29 is further comprised of eyeball 33, cornea 35 and sclera 34. An upper cul-de-sac 37 and a lower cul-de-sac 38 are defined by a conjunctiva 39. Ocular drug delivery device 10 is positioned in lower cul-de-sac 38 to continuously dispense a metered amount of a drug or a combination of drugs from the device to the eye and its surrounding tissues over a prolonged period of time. In medical operation, after drug leaves the ocular drug delivery device, it is transported to the eye and its surrounding tissues, by physiological processes such as the flow of tear liquid, blinking action of the eyelids, and the like.

Figure 7:
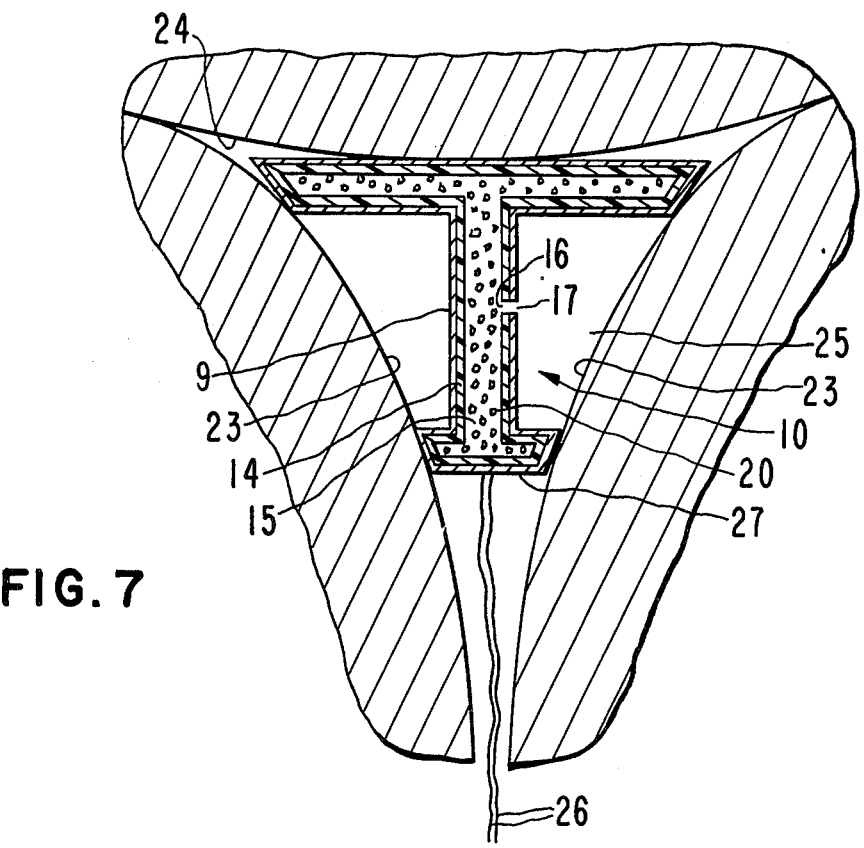
FIG. 7 is a frontal, fragmentary view of a uterine cavity showing an agent releasing intrauterine device manufactured in accordance with the invention and positioned in a uterine cavity.

In FIG. 7 there is graphically depicted another product dispensing device 10 fashioned as an intrauterine contraceptive antifertility delivery device prepared according to the spirit of the invention. Device 10, in this embodiment, is of letter "H" configuration and it is adapted to be located within a uterine cavity and it contacts the sides 23 as well as the fundus uteri 24 of uterus 25. Thread 26 is attached to the trailing end 27 of device 10 for manually removing it from uterus 25. Device 10 is comprised of a wall 14 formed of a semipermeable membrane surrounding a compartment 15. A passageway 16 serves as a conduit for the movement of drug 20 from compartment 15 through opening 17 into uterus 25. Compartment 15 is comprised of an antifertility agent 20 that may be soluble in uterine fluid that enters the compartment through the wall 14 and exhibits an osmotic pressure gradient against the fluid, or agent 20 can have limited solubility such as slightly soluble or moderately soluble in uterine fluid confined in the compartment and have mixed therewith either homogenously or heterogenously, as osmotically effective solute that is soluble in uterine fluid and exhibits an osmotic pressure gradient against external uterine fluid. Wall 14 is formed of a semipermeable material that lets fluid permeate into chamber 15 at a rate controlled by the permeability of the material. Wall 14 is layered distant from 15 with release rate profile material 9 formed of a hydrophobic material that erodes at a controlled rate over a prolonged period of time in response to the pH of the uterus. The term hydrophobic or hydrophobicity as used herein broadly refers to a material that does not absorb or adsorb appreciable amounts of water. The term includes materials which adsorb or absorb water in a maximum amount usually not exceeding 10% of its dry weight. The thickness of the coating on the device can vary and it usually is from 0.01 to 75 mils, or higher. In operation, intrauterine device 10 in one embodiment is comprised of a layered 9 semipermeable wall 14 having its compartment charged with a mixture comprised of the antifertility agent progesterone that has limited solubility in an aqueous medium and an aqueous soluble, osmotically effective solute that exhibits an osmotic pressure gradient against the aqueous medium, that is uterine fluid. Device 10 when positioned in a uterine cavity releases antifertility agent at release rate profile determined by the erosion rate of coat 9 and then at a zero order rate of release within the device's control to the uterine cavity throughout the major portion of the device's medical history. An insoluble antifertility drug 20 also can be used in a form that is soluble in uterine fluid but physiologically inactive until its release from the device to the uterine cavity wherein it is converted by the uterus and its surrounding tissues, such as the endometrium, myometrium and the like, to a physiologically antifertility active compound. When a soluble form of an antifertility drug is used, it serves as the osmotic solute eliminating the need for an additional solute. Antifertility drug is released through passageway 16 in the fluid that permeates through the exposed semi-permeable wall producing the osmotic solute containing, in the case of a drug of limited solubility, undissolved and some dissolved antifertility agent which is released at an osmotic rate that corresponds to the rate controlled by the permeability of the membrane to the fluid and the osmotic attraction to the fluid as expressed by the osmotic pressure gradient across the exposed semi-permeable wall.

Figure 8:
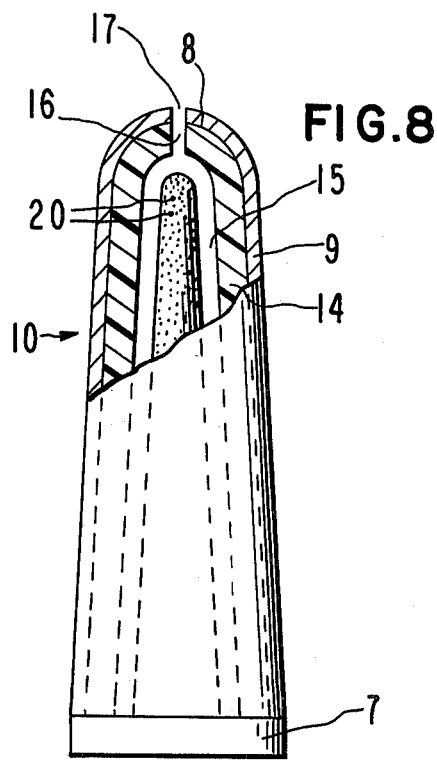
FIG. 8 is still another embodiment of the invention illustrating a side, fragmentary view of an anal osmotic drug delivery device for releasing a drug in a body cavity.

FIG. 8 illustrates another product delivery device 10 of the invention. In FIG. 8, delivery device 10 is designed for administering a drug 20 within a body opening, the anal canal, not shown. Product delivery device 10 is comprised of a semi-permeable film 14 coated with a release rate pattern governing material 9 and it is shaped like an obelisk with a lead end 8 and a tailing end 7. Wall 14 surrounds a product compartment 15 which serves as a reservoir for drug 20. Reservoir 15 is comprised of drug 20 in solid form that can be released from device 10 at a metered rate over a prolonged period of time. Wall 14 is suitably formed with a passageway 16 terminating in an outlet 17 for releasing drug from device 10. Wall 14 can be isotropic, wherein the structure is homogenous throughout the cross-section of the wall, or wall 14 can be anisotropic wherein the structure is non-homogenous. Coating 9 on wall 14 of this device is uniform in thickness from lead end 8 to trailing end 7 and it is selected from a non-toxic, physiological, inert material that bioerodes in the environment of use. In this osmotic suppository device, as with the devices discussed above, drug is released by the operation of the device as fully described in the earlier devices.

Figure 9:
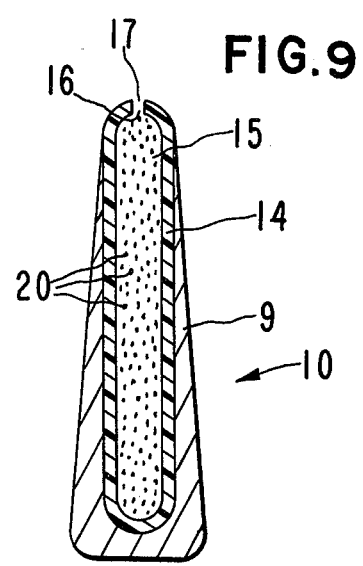
FIG. 9 is similar to FIG. 8 except the exterior coat carried on the wall increased in thickness from the passageway to the bottom of the device.

FIG. 9 presents another osmotic agent delivery device 10 of the invention. In FIG. 9, device 10 is designed for releasing agent 20 within an animal body opening such as the anal canal or the vagina, not shown. Osmotic agent delivery device 10 is comprised of a semipermeable wall 14 coated with an erodible time release profile material 9 and the device as shown has an elongated shape. Semipermeable wall 14 surrounds an agent compartment 15 for containing agent 20. Wall 14 is formed with a passageway 16 terminating in outlet 17 for releasing agent from device 10. Coating 9 on semipermeable wall 14 is made from a bioerodible material and it can be of uniform thickness from the top to the bottom of device 10, or it can increase or vary in thickness from the top to the bottom of device 10. By applying coat 9 of uniform or varying thickness, from film to layer, different time release profiles such as increasing, pulsing, sinusoidal, and the like are obtained. These profiles are obtained as coat 9 gradually erodes at a predetermined rate in fluids exposing coextensive extremities of semipermeable wall 14 for passage of fluid into compartment 15. The profiles are also obtained by coat 9 continuously surface eroding to control the passage of fluid through a permeable coat 9 for regulating the amount of fluid available to wall 14 for imbibition.

The embodiment of the invention as set forth in FIG. 9 makes possible many programs of therapy that require different quantities of medication administered at varying times. For example, in antibiotic therapy, an initially large dose of drug can be administered followed by smaller doses. Also, in desensitizing against allergens, the therapeutic regime indicates doses of the allergen to progressively increase over the time of treatment is now possible with the devices of this invention. Thus, as the coating gradually erodes or dissolves at a predetermined rate in the body fluids, it lets fluid contact the semipermeable wall to obtain preselected release patterns with the devices made according to the mode and manner of the invention.

In FIG. 10 the present invention is seen in another operative embodiment comprised of a controlled release device 10 for releasing medication at a zero order rate to a preselected environment. Device 10 is suitably adapted for the oral administration of a medication to humans, primates, laboratory animals, farm animals, household animals, avians and sport animals. Device 10 is comprised of a wall 14 formed either fully or in at least a part of a semipermeable film forming membrane that surrounds medication. A layer 9 of constant or varying thickness that erodes or undergoes dissolution in the gastrointestinal tract is coated onto the exterior of wall 14. Layer 9 can be an enteric coat which is not disintegrated in the stomach but readily undergoes dissolution in the upper intestinal tract, or it can be a material that gradually and continually erodes or undergoes dissolution as the device travels through the gastrointestinal tract. A passageway 16 releases medication to the exterior of the device. Device 10 has at least one passageway and it can have additional passageways to release the same amount of drug or more drug at various osmotic pumping rates to the host or the environment. In FIG. 11, device 10 of FIG. 10 is seen in open section illustrating semipermeable, non-digestible, non-toxic, biologically inert wall 14 surrounding drug 20 and passageway 16. A time release profile layer 9, is carried on wall 14. The amount of drug 20 in the osmotic device will, of course, vary with the host and the length of time it is to remain in the host before it is discharged from the body.

The amount of agent present in the just described osmotic device, and similar devices, is initially in excess of the amount that can be dissolved in the fluid present in the interior of the device. Under this physical state, that is, when the agent is in excess, the device will osmotically operate to give essentially zero order rate of release. The rate of agent release pattern can also be varied by selecting different amounts of agent that can be confined in the agent compartment, that is, smaller or larger amounts than is soluble in the fluid in the compartment may be housed therein. Thus, the device can contain from 0.05 mg to 25 grams or higher with individual devices containing for example 1 mg, 5 mg, 10 mg, 100 mg 250 mg, 500 mg, 1.5 g, 3 g, 5 g, and the like. In FIG. 12 device 10 is seen comprised in operation in an outline of a human 28 in stomach 29 osmotically administering drug 20 to the drug receptor.

Figure 14:
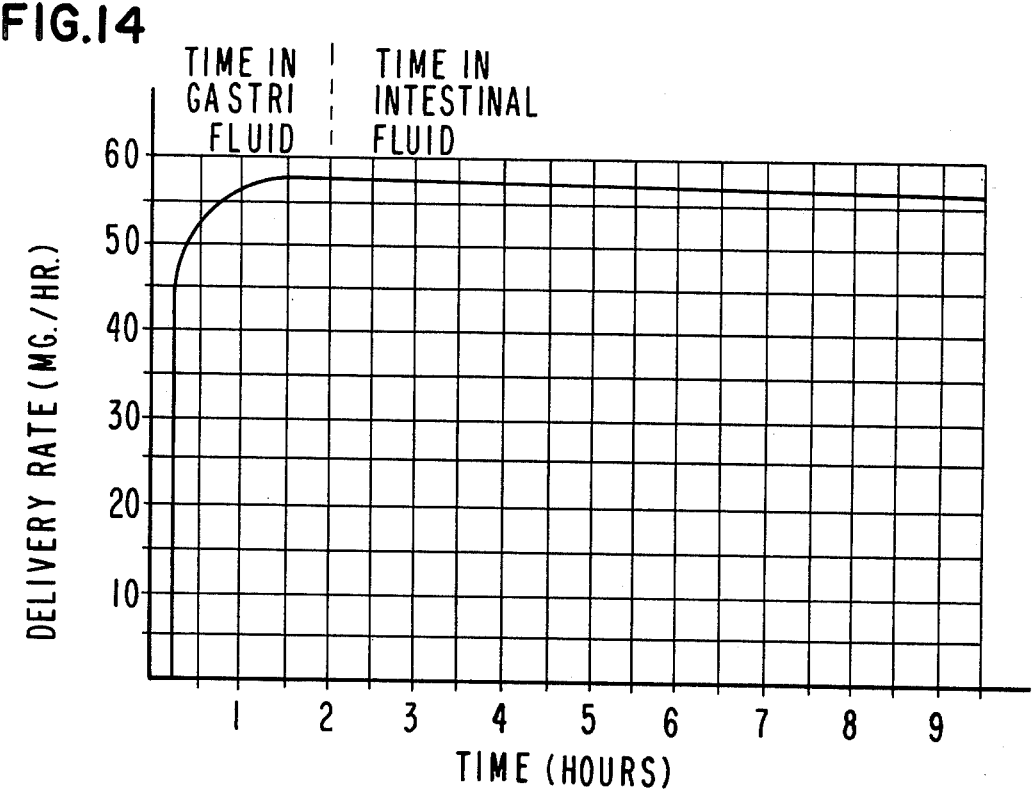
FIG. 14 illustrates a device releasing active agent independent of the pH of the exterior of the device.
Figure 15:
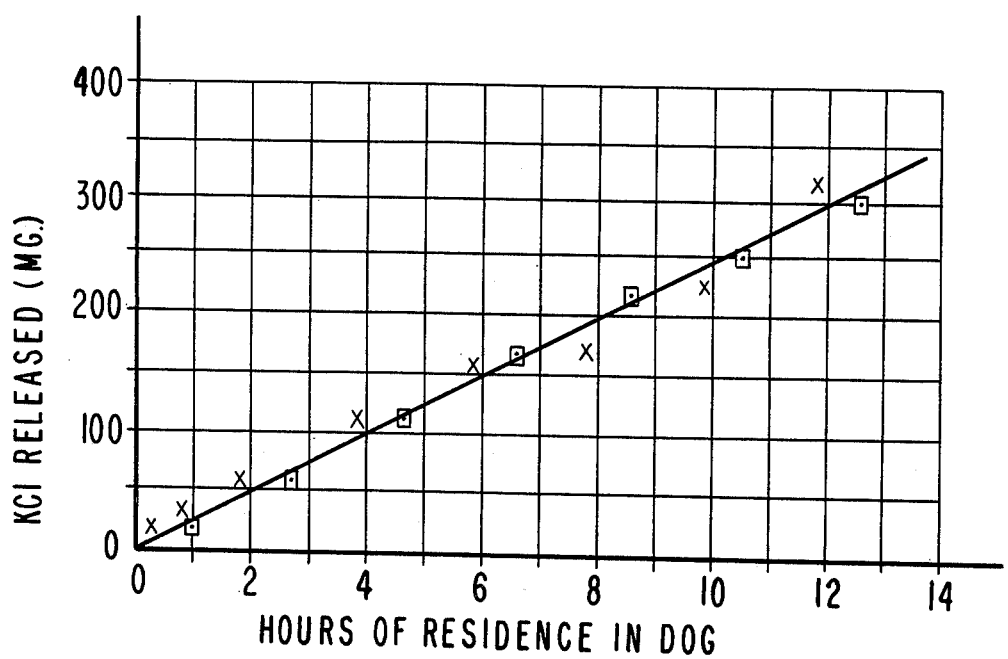
FIG. 15 illustrates in vivo results obtained by using the device.
Figure 16:
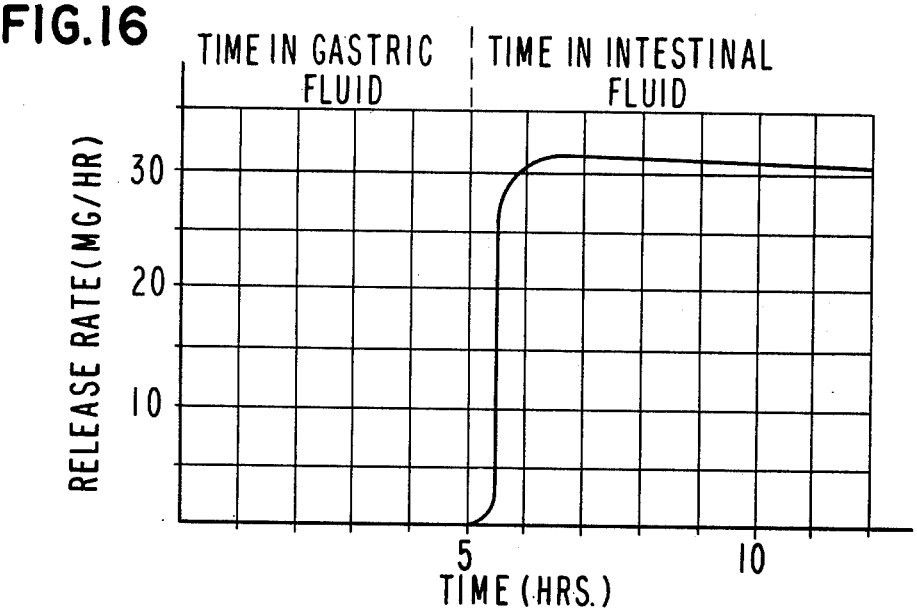
FIG. 16 illustrated an oral drug delivery device manufactured to release drug in a selected biological environment, the intestine.
Figure 17:
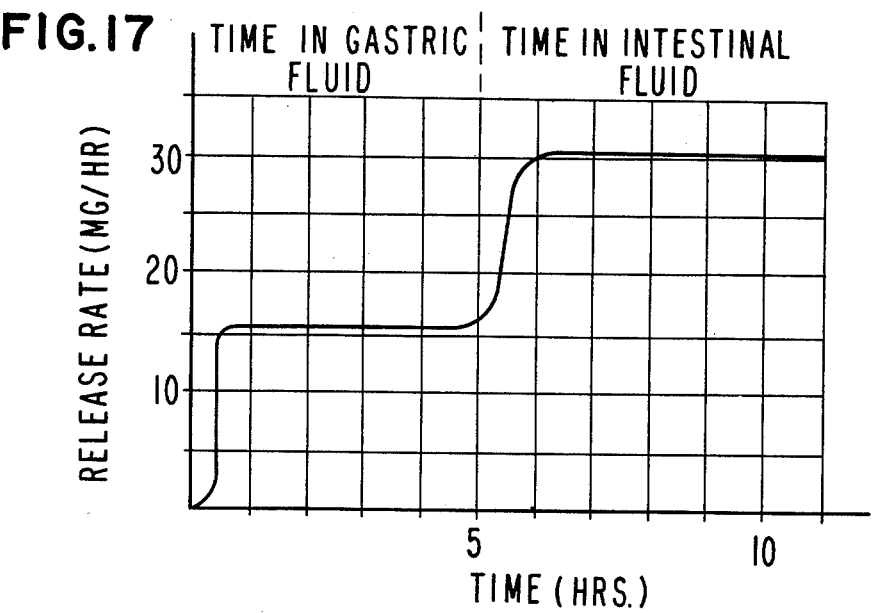
FIG. 17 illustrates a drug delivery device of the invention illustrating a device having different drug release rate patterns in two different biological environments.
Figure 18:
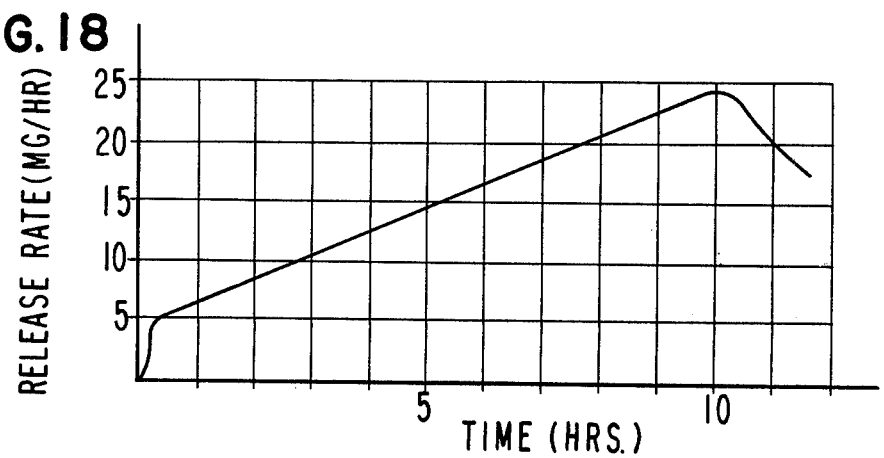
FIG. 18 depicts an osmotic agent releasing device where the exterior coat continually erodes to give an incrementally increasing time release rate profile for the device.

In FIG. 13 there is presented a graph illustrating an essentially zero order rate of release for an osmotic device made according to the invention. This release pattern is obtained by coat 9 instantly eroding to expose semipermeable wall 14 to let fluid permeate therethrough to release agent from device 10. This coat protects the device during storage and the like. In FIG. 14 there is seen a graph depicting an osmotic device releasing drug at a contant rate independent of the pH of the exterior fluid. The device releases agent at this release rate profile after dissolution of coat 9 to expose the semipermeable wall. The two fluids mentioned on the graph are gastric fluid and intestinal fluid. The gastric fluid had a pH of about 1 to 2 and the intestinal fluid had a pH of about 7 to 8. FIG. 15 shows an osmotic device delivering potassium chloride throughout the gastrointestinal tract of dogs. The rate of release for the device during the first 2 hours was ascertained by assaying devices recovered from the stomach; while, the rate delivered at longer terms was determined by evaluating devices recovered from the intestines. FIG. 16 illustrates the results obtained with a device coated with an enteric coat that prevents agent release in the stomach but erodes to give a zero order rate of release in the intestine. FIG. 17 illustrates the release rate profile for a device coated with a material that has a changing release rate profile. This graph illustrates one release rate profile in the stomach with subsequent erosion to give a second release rate profile in the intestine. FIG. 18 illustrates the release rate profile obtained as a coat 9 gradually and continually erodes to expose more wall to give the corresponding increased release rate profile.

While the above FIGS. 1 through 18 inclusive are illustrative of various operative, osmotic agent delivery devices that can be made according to the invention, it is to be understood that these delivery devices of the invention can take a wide variety of shapes, sizes and forms for administering, for example, the useful agent, drug, product or the like at controlled rates at different release rate profiles to different areas, for example, of the body or to different drug receptor sites or to animal body passages or for administering other active agents to other environments. For example, the invention includes oral drug delivery devices such as tablets, pills and capsules, vaginal delivery devices, osmotic implants, osmotic buccal devices, pessaries, prosthesis, artificial glands, cervical rings, intrauterine drug delivery devices of cylindrical, bullet, elliptical, circular, bulbous, loops, bows, or any other geometrical shape that readily lends itself to intrauterine placement such as Birnberg's Bow in U.S. Pat. No. 3,319,625, Comet in U.S. Pat. No. 3,256,878, Majzlin Spring in U.S. Pat. No. 3,397,691, Inhiband in U.S. Pat. No. 3,323,520, Bakunin in U.S. Pat. No. 3,405,711, Shamrock in U.S. Pat. No. 3,077,879, the ring with tail, Ota ring and the like. The devices also include osmotic ocular drug delivery devices of any convenient geometric shape for comfortable retention in the cul-de-sac of the eye such as ellipsoid, bean-shaped, banana-shaped, circular-shaped, rectangular-shaped, trapezoidal, doughnut-shaped and the like. In cross-section, it can be doubly convex, concavo-convex, rectangular and the like, as the osmotic ocular device in operation will tend to conform to the configuration of the eye. The general dimensions of the osmotic ocular device can vary with the size of the device and conforming to the amount of agent in the device's agent compartment, the rate at which the agent is to be administered to the eye and by the size of the eye. Satisfactory devices for insertion in the cul-de-sac of the eye generally have a length of 4 to 20 millimeters, a width of 1 to 15 millimeters, and a thickness of 0.1 to 4 millimeters, a reservoir with a diameter of 1.2 to 14.9 millimeters, and contain from 1 microgram to 100 milligrams of drug or more, and the like. The ocular drug delivery device can be made of a material that is biologically inert, non-allergenic and essentially insoluble in tear fluids, or it can be made from a bioerodible, non-allergenic material that erodes after it has fulfilled its drug release therapy. The oral osmotic tablets made according to the invention can also be of various conventional sizes such as 3/16 in, 7/32 in, 11/32 in, 7/16 in, ½ in, ¾ in, 1 in, 1¼ in, 1⅜ in, 2⅛ in, 2½ in and the like smaller or larger dimensions. The oral tablet can also have an elongated shape with a size corresponding to conventional capsule dimensions such as triple zero, double zero, zero, 1 through 8 and the like. Additionally, the novel and useful dispensing device can be used for release of a wide variety of active agents and the term agents as used in this specification and the accompanying claims includes any compound, mixture of compounds, composition of matter or mixture thereof, product, drug, which, when dispersed, produces a predetermined beneficial and useful result. The active agents include pesticides, herbicides, germicides, biocides, algicides, rodenticides, fungicides, insecticides, anti-oxidants, plant growth promotors, plant growth inhibitors, preservatives, surfactants, disinfectants, sterilization agents, catalysts, chemical reactants, medicants, fermentation agents, cosmetics, foods, nutrients, food supplements, plant food, drugs, vitamins; plant minerals, six sterilants, plant hormones, fertility inhibitors, fertility promotors, air purifiers, micro-organism attenuators, and other like agents that benefit man, animals, avians, fish and the environment. Also, all of the dispensing devices are of appropriate known shapes and sizes for implantation, insertion or positioning in the desired body cavities, passageways or in the desired environment, such as streams, aquariums, fields, reservoirs, laboratory facilities, manufacturing facilities, transport means and the like.

DETAILED DESCRIPTION OF THE DISCLOSURE

In accordance with the practice of the present invention, it has now been found that the novel delivery device of the invention provides many important advantages over previously-known dissolution operated, diffusional operated, sustained and prolonged delivery devices, of both the non-erodible or bioerodible type and the like. One advantage of the novel device is the ease of construction of the drug delivery device by standard manufacturing techniques into devices of various shapes, sizes and forms for delivering products to a recipient or environment. A more important advantage of the claimed delivery device is that it can be manufactured comprised of a minimum number of parts, that is, a wall and a composition of matter. Another important advantage resides in the ability to manufacture the devices of the invention by standard, conventional methods of manufacture. Another important advantage is the present and future ability of the device to contribute to the art different release rate profiles, with zero order rate of release, or other order rate of release within the various release rate profiles. Other advantages will become apparent to those versed in the art from the specification, the drawings and the accompanying claims.

The wall 14, forming the osmotic device of the invention is made from a material that is semi-permeable, can form films, and does not adversely effect the drug, animal body, or the host. For example, it is a material that is permeable to an external fluid such as water and the like while essentially impermeable to a selected product, drugs, agents or to other compounds in the device. The selectively-permeable material or membrane forming the wall is insoluble in body fluids and non-erodible or it can be bioerodible after a predetermined period with bioerosion corresponding to the end of the active drug release period or release of agent to the environment of use. In each instance it is semi-permeable to external solvent but not to solute and is suitable for construction of the osmotic powered device. Typical materials for forming the wall include membranes known to the art as osmosis and reverse osmosis membranes such as commercially-available unplasticized cellulose acetate, plasticized cellulose triacetate, agar acetate, amylose triacetate, beta glucan acetate, beta glucan triacetate, cellulose acetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose ethers, cellulose acetate propionate, poly(vinyl methyl) ether copolymers, cellulose acetate diethylaminoacetate, cellulose acetate octate, cellulose acetate laurate, methyl cellulose, cellulose acetate p-toluene sulfonate, triacetate of locust gum bean, cellulose acetate with acetylated hydroxyethyl cellulose, hydroxylated thylenevinylacetate, cellulose acetate butyrate having a viscosity of from about 10 seconds to about 50 seconds, cellulose acetate butyrate containing about 17 percent of combined butyryl and about 29.5 percent acetyl, permselective, aromatic nitrogen-containing polymeric membranes that exhibit water permeability and essentially no solute passage, osmosis membranes made from polymeric epoxides, osmosis membranes made from copolymers of an alkylene oxide and alkyl glycidyl ether, semi-permeable polyglocolic or polylactic acid and derivatives thereof, the selectively-permeable membranes of ionically associated polyelectrolytes, the selectively-permeable polymers formed by the coprecipitation of polycation and a polyanion as described in U.S. Pat. Nos. 3,276,586; 3,541,005; 3,541,006; 3,546,142; and 3,173,876; and the like. Generally, membranes having a fluid permeability of 0.01 to 10 cc/cm$^2$ × hour or day/or higher at atmospheric pressure against a saturated product solution or saturated solute solution at the temperature of use while simultaneously possessing a high degree of impermeability to the product or solute are useful for manufacturing the devices of the invention. Also, among the suitable semi-permeable membranes operable for the purpose of the invention are film forming membranes that possess a water sorption greater than one percent and less than 40 percent by weight at ambient temperatures with a presently preferred semi-permeable membranes having a water sorption of greater than 5 and less than 30 percent by weight at ambient temperatures. Of course, other semi-permeable membranes operable for the purposes of the invention can also be used within the spirit of the invention.

The coating 9, carried on the semi-permeable wall 14 can comprise suitable materials for the purpose of this invention. One class of suitable materials are the enteric coatings that give a predetermined release rate profile by resisting the action of stomach fluid to prevent water permeating through the wall, while disintegrating in the intestine to let fluid enter the device. Acceptable enteric coatings are non-toxic, the components of the coating and their degradation product should be physiologically inactive, the coating should not dissolve or disintegrate in the stomach during the time the device remains in the stomach, and, the enteric coating should disintegrate to expose the semi-permeable wall once the device enters the intestine. The enteric coating suitable for the present invention include those materials digestible by the enzymes in the intestinal tract and materials containing an ionizable polyacid, frequently a long-chain polymer with ionizable carboxyl groups, and the like. Typical materials for forming enteric coating include keratin, keratin over sandaractolu, $\beta$-naphthyl benzoate and acetotanin, balsam of peru, balsam of tolu, stearic acid and shellac, gum resin and salol-shellac formalized gelatin, cellulose ester and a non-volatile organic substance such as fat, wax or bile, cellulose ether and fat, wax or bile, fatty acids, myristic acid-hydrogenated castor oil, stearic acid-mutton tallow or sodium taurocholate, stearic acid-castor oil over shellac-silica gel, shellac, ammoniated shellac, shellac n-butyl stearate, amstic with cetyl alcohol, cellulose acetate phthalate with resinous carrier, polyvinyl acid phthalate, methylcellulose acid phthalate, acid phthalates of glucose, fructose or mannitol, zein, alkyl resin unsaturated fatty acids shellac, hippuric acid with and without cetyl alcohol, styrene maleic acid copolymer and combinations containing dibutyl phthalate and talc, ternary copolymers of styrene, methacrylic acid with butyl half-ester of maleic acid, and the like. Typical enteric coatings are discussed in *Remington's Pharmaceutical Sciences*, Thirteenth Ed., pages 604 to 605, 1965 Mack Publishing Co., Eaton, Penna.; and in *Biopharmaceutics and Relevant Pharmacokinetics*, First Ed., pages 158 to 165, 1971 Drug Intelligence Publications, Hamilton, Ill.

The coating 9 carried on wall 14 can also be made of a material that gradually erodes at a predetermined rate in body fluids to expose wall 14 to fluid or it erodes and becomes thin to let fluid diffuse through to wall 14. By adjusting the thickness of the coating and desired release profile can be programmed. Exemplary materials include those materials which slowly dissolve in body fluids, and coating materials that hydrolize in body fluids for example, the polymeric essentially linear, dibasic acid anhydride of the formula

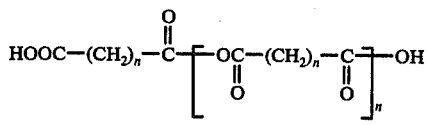

are also suitable for use as coatings herein. Typical coatings include polyanhydride polymers of sebacic and azelaic acid, polyhydroxyacetic acids as described in U.S. Pat. Nos. 2,668,162 and 2,676,945, and polysulfite polymers. Other polymers useful for coatings include polymers cleaved by enzymes present in body fluids such as chitin which is enzymatically cleaved by lysozyme, and the like.

Coating 9 can also be a release rate profile material comprised of a hydrophobic poly(carboxylic acid) having an average of one ionizable hydrogen for each 8 to 22 carbon atoms. These polyacid coatings erode in response to the essentially constant pH environment at a controlled rate by a process of carboxylic hydrogen ionization. This erosion extends over a prolonged period of time and exposes the semi-permeable wall over a corresponding prolonged period of time. Exemplary poly(carboxylic acids) materials useful as coatings are the hydrophobic polyacids which are represented by the general formula:

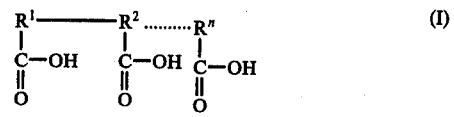

wherein the R's are organic radicals independently selected to provide, on average, from 8 to 22 total carbon atoms for each carboxylic hydrogen. Variations of this ratio within this range can vary the erosion rates prepared from these polymeric acids. Organic radicals represented by $R^1$, $R^2$ ... $R^n$ may be selected from hydrocarbon radicals and heteroatom containing organic radicals. Suitable hetero atoms for employment in $R^1$, $R^2$ ... $R^n$ include oxygen, nitrogen, sulfur, and phosphorous as well as other hetero atoms. The value of $n$ and hence the average molecular weight of the polymer is not critical and may vary over a wide range. Suitable molecular weights, for example, range from about 10,000 to about 800,000. Materials within this range erode to products which may be easily and innocuously passed from the environment of use. Preferred molecular weights are from about 15,000 to about 500,000.

Suitable polymeric coatings of the polyacid type are prepared from monomers that contain polymerizable olefinic carbon-carbon double bonds, wherein at least a portion of these monomers will have bonded thereto one or more carboxyl radicals, or suitable precursors thereof and optionally other hetero atom radicals. The polymer is synthesized by the addition of these monomers, one to another, across the polymerizable double bonds. This general method for forming polyacids is well known and does not comprise a part of the present invention. This preparative method may be generally represented by the reaction:

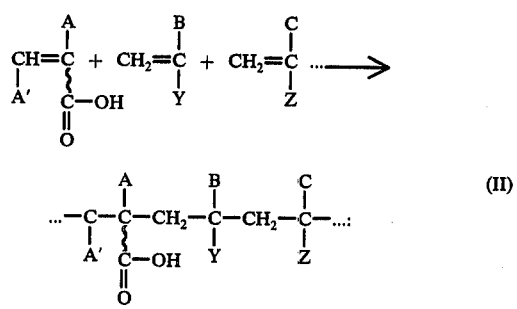

wherein A represents hydrogen or a hydrocarbon and

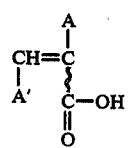

represents a carboxyl group, or carboxyl group precursor containing monomer also containing a polymerizable olefinic double bond. Such monomers include, for example, acrylic acid, substituted acrylic acid, maleic acid, maleic anhydride, crotonic acid and the like. Wherein

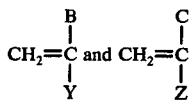

represent organic monomers containing a polymerizable double bond which may be the same or different than

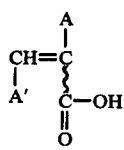

This preparative technique can be employed to prepare poly(carboxylic acids) in accord with General Formula I having hydrocarbon R's either by polymerizing suitable hydrocarbon substituted acrylic acids and crotonic acids or by copolymerizing olefinically unsaturated acids, such as acrylic acid or hydrocarbon-substituted acrylic acids or the crotonic acids, with unsaturated hydrocarbons. Suitable poly(carboxylic acids) having hydrocarbon R's prepared by polymerizing substituted acrylic acids may be represented by the general formula III:

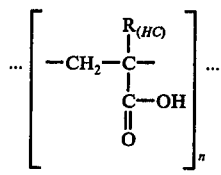

wherein $R_{(HC)}$ represents hydrocarbon substituents averaging from 5 to 15 carbon atoms in size, for example n-pentyl, cyclohexyl, phenyl, n-decyl, 2,2-diethyldecyl, combinations of butyl and hexyl, and the like. Such materials may be prepared by polymerizing the corresponding hydrocarbon substituted acrylic acid monomers with free radical initiators as described in U.S. Pat. No. 2,904,541.

The coatings of poly(carboxylic acids) also are prepared by copolymerizing unsaturated carboxylic acids such as acrylic acid (or substituted acrylic acid) with a polymerizable hydrocarbon. These acids may be represented by the general formula:

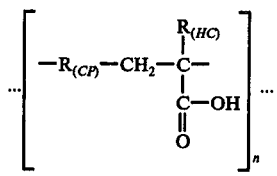

wherein $R_{(HC)}$ is a hydrocarbon radical of up to about 12 carbons or hydrogen; and $R_{(CP)}$ is a copolymerized hydrocarbon group. The hydrocarbons which may be copolymerized with unsaturated carboxylic acids include terminally olefinically unsaturated hydrocarbons and olefinically unsaturated hydrocarbons having a conjugated carbon-carbon double bond. Typical hydrocarbon groups represented by $R_{(CP)}$ include ethyl, propyl, butyl, isopentyl, and phenylethyl, as result when ethylene, propylene, butadiene, isoprene and styrene, respectively, are copolymerized with unsaturated acids. These preparations are set forth in J. Poly. Sci. 10, 441, (1946 Series) and J. Poly. Sci. 10, 597 (1946 Series).

The poly(carboxylic acids) coatings embrased by general formula I having hydrocarbon R's may also be prepared by other known techniques, such as for example by oxidizing terminal methyl groups on suitable hydrocarbon polymers to carboxyl groups with alkaline permanganate as described in Cram and Hammond Organic Chemistry, Second Ed., pages 525 to 526; or by carboxylating olefinically unsaturated hydrocarbon polymers by contacting them with carbon monoxide, water and optionally some hydrogen under conditions of elevated temperature and pressure in the presence of strongly acidic catalysts, for example HF, $BF_3$, $H_2SO_4$ and the like.

Polycarboxylic acids useful as coatings for the devices of the invention and illustrated by general formula I may suitably incorporate oxygen atoms in their R's. Oxyhydrocarbon R's include ester groups or ether groups. Poly(carboxylic acids) represented by Formula I incorporating ester groups, as R's, are especially suitable coatings as used herein. They may be readily prepared by partially esterifying acid polymers or copolymers, which are themselves easily obtained. They offer the advantage of permitting simple variation of the ratio of carbons to ionizable carboxylic hydrogens by varying the extent of partial esterification or the esterifying alcohol employed. As a result, easy adjustment of erosion characteristics of the poly(carboxylic acid) product and hence a predetermined release rate profile is obtained.

A typical example of a release rate profile aqueous permeable coating for use in aqueous enviroments where the presence of organic media is essentially very low, is seen in the case of poly(acrylic acid). Poly(acrylic acid) is available commercially or may be easily prepared such as by mixing 167 parts of 60% acrylic acid, 232 parts of water, 0.50 parts of potassium peroxydisulfate and 0.25 parts of potassium metabisulfite and heating the mixture to 60° C. Also, coating can be prepared by using half the carboxyl groups of poly(acrylic acid) which are esterified by reaction with a hexanol. The resulting partial ester is hydrophobic and has a carbon to ionizable hydrogen ratio within the range necessary for materials employed in the devices of this invention, for example, 12:1. A similarly suitable material would result if two-thirds of the poly(acrylic acid) carboxyl groups were esterified with ethanol.

This partial esterification technique for obtaining coating is of course not limited to treatment of acrylic acids. Any organic lower poly(carboxylic acid) may be partially esterified when necessary to achieve the required hydrophobicity and carbon to acidic hydrogen ratio. Other polyacids which often benefit from esterification include homopolymers of unsaturated lower carboxylic acids such as the lower alkyl acrylic acids, for example methacrylic and ethacrylic acid; crotonic and propiolic acid; maleic acid and fumaric acid. Polymers of acid precursors such as poly (maleic anhydride) may be hydrolyzed and partially esterified as well. Also suitable for esterification are acids or precursors copolymerized with lower unsaturated hydrocarbons of from 2 to 8 carbons such as ethylene, propylene, butadiene, styrene and the like, or with lower unsaturated oxyhydrocarbons such as unsaturated ethers of from 3 to 8 carbon atoms. Many of these polymers and copolymers are available commercially. Others can be prepared by bulk, solution, emulsion or suspension polymerization using free radical initiators at 40°–100° C, all methods well known in the art. The partial esterification may be conveniently carried out by contacting the acid-containing polymers with a controlled quantity of the esterifying alcohol at elevated temperature, optionally in the presence of an acidic esterification catalyst. Alcohols suitable for partially esterifying the above-noted polyacids include the hydrocarbon alcohols, preferably the alkanols of from about one to about 16 carbon atoms; for example, methanol, ethanol, isopropanol, n-butanol, cyclohexanol, octanol, the decanols, and n-dodecanol. Combinations of alcohols may also be employed. In general formula I the ether groups may be incorporated by copolymerizing an unsaturated carboxylic acid with an unsaturated ether, for example, acrylic acid, maleic acid, crotonic acid and the like with the vinyl ethers of from about 3 to about 10 carbon atoms such as methyl vinylether, ethyl vinyl ether, butyl vinyl ether, hexyl vinyl ether and the like, for example by the method described in U.S. Pat. No. 2,927,911. Because of the small number of carbon atoms in many of these unsaturated ethers and acids it may be desireable, to achieve the required carbon/acidic hydrogen ratio, to terpolymerize these materials with a non-carboxylic hydrogen-containing material, most suitably an unsaturated terpolymerizable unsaturated hydrocarbon of from 2 to 8 carbon atoms such as ethylene, butadiene, or styrene.

The coatings embraced by the R's of general formula I, as oxyhydrocarbons may also contain alcohol linkages. Additionally, nitrogen sulfur and phosphorous atoms may also be incorporated in R groups employed in the polymer coatings. Nitrogen may be present as cyano, amide, or imide groups. Sulfur atoms can be present as mercaptan or disulfide linkage while phosphorous atoms may be present as phosphate linkages.

One group of coating materials used to coat the osmotic dispensing device of the invention comprise hydrophobic polymers of an acid selected from acrylic acid, lower alkyl acrylic acids of from 4 to 6 carbon atoms per monomeric unit, and maleic acid; either alone or copolymerized with up to about 2 moles, per mole of acid of a copolymerizable olefinically unsaturated group such as ethylene or lower such as 1 to 4 carbon, alkyl vinyl ethers wherein from about 20 to 90% of the acid groups have been esterified with an alkanol of from 1 to about 10 carbon atoms and wherein the ratio of total carbon atoms to acidic carboxylic hydrogens is in the range of from about 9:1 to about 20:1. Also, suitable coatings include the hydrophobic partially esterified copolymers of acrylic acid, methacrylic acid or maleic acid with from 0.2 to 1.5 moles, per mole of acid of ethylene or lower (1–4 carbon) alkyl vinyl ether having from about 35 to about 70% of their total carboxylic groups esterified with lower alkanol of from about 3 to about 10 carbon atoms, said copolymers having a carbon to acidic carboxylic hydrogen ratio of from about 10:1 to about 15:1. Coat 9 further includes hydrophobic copolymers of maleic acid with about 1 mole, per mole of maleic acid, of ethylene or methyl vinyl ether, said copolymer having about half of its total carboxyl groups esterified with a lower monalkanol of from 4 to 8 carbon atoms, wherein the carbon to acidic carboxylic hydrogen ratio has a value of from about 10:1 to about 14:1, and the like. Other time delay materials include fatty acids having 10 to 22 cargbns, fatty alcohols having from 14 to 30 carbons, the esters of mono-, di-, or triglyceryl esters formed from fatty acids having 10 to 22 carbon atoms, silicone and substituted silicone derivatives and the like.

Representative of agent that can be released from the device and can function as a solute are without limitation those agents soluble in fluids inside the compartment. The fluid is originally present in the environment of use in various forms, for example, such as an aqueous type fluid such as tear fluid, tissue juices, extra-cellular fluid, intra-cellular fluid, water, organic solvents, mixed solvent systems and the like. The expression "agent" as previously noted and as used in this disclosure is meant to include the terms product, useful active agent, beneficial agent, drug, composition of matter, and the like, and these terms are deemed as functionally equivalent for the present invention. These agents, in one embodiment, are both useful to environment or host and preferably osmotically effective as solutes since they can generate a solvent concentration gradient between the exterior medium and the medium inside the device. In the specification and the accompanying claims, useful active agent embraces the term "drug" and broadly includes physiologically or pharmacologically active substance for producing a localized or systemic effect or effects in mammals including humans and primates, avians, valuable domestic household, sport or farm animals such as sheep, goats, cattle, horses, etc., or for administering to laboratory animals such as mice, rats, guinea pigs and the like. That is, the novel osmotic drug delivery device can be used for administering drugs that are physiologically or pharmacologically active at a point in near relation to the osmotic drug delivery device, or, for administering a systemically active substance which will produce a physiological or pharmacological response at a site remote from the point of application of the osmotic drug delivery device. The active agents that may be administered include inorganic and organic compounds without limitation, those materials that transport across a vessel, for example, drugs acting on the central nervous system such as hypnotics and sedatives, mixtures thereof such as pentobarbital sodium, phenobarbital, secobarbital, thiopental, etc., heterocyclic hypnotics such as dioxopiperidines, and glutarimides, hypnotics and sedatives such as amides and ureas exemplified by diethylisovaleramide and α-bromo-isovaleryl urea and the like, and hypnotic and sedative urethanes, disulfanes and the like, psychic energizers such as isocarboxazid, nialamide, phenelzine, imipramine, tranylcypromine, pargylene and the like, tranquilizers such as chloropromazine, promazine, fluphenazine reserpine, deserpidine, meprobamate, benzodiazepines such as chlordiazepoxide and the like, anticonvulsants such as primidone, diphenylhydantoin, ethltoin, pheneturide, ethosuximide and the like, muscle relaxants and anti-parkinson agents such as mephenesin, methocarbomal, trihexylphenidyl, biperiden, levodopa, also known as L-dopa and L-β-3-4-dihydroxyphenylalanine, and the like, analgesics such as morphine, codeine, meperidine, nalorphine and the like, antipyretics and anti-inflammatory agents such as asprin, salicylamide, solium salicylamide and the like, local anesthetics such as procaine, lidocaine, naepaine, piperocaine, tetracaine, dibucane and the like, antispasmodics and antiulcer agents such as atropine, scopolamine, methscopolamine, oxyphenonium, papaverine, prostaglandins such as $PGE_1$, $PGE_2$, $PGF_{1\alpha}$, $PGF_{2\alpha}$, PGA and the like, anti-microbials such as penicillin, tetracycline, oxytetracycline, chlorotetracycline, chloramphenicol, sulfonamides and the like, anti-malarials such as 4-aminoquinolines, 8-aminoquinolines and pyrimethamine, hormonal agents such as prednisolone, cortisone, cortisol and triamcinolone, androgenic steroids, for example, methyltestosterone, fluoxmesterone and the like, estrogenic steroids, for example, 17$\beta$-estradoil and thinyl estradiol, progestational steroids, for example, 17$\alpha$-hydroxyprogesterone acetate, 19-nor-progesterone, norethindrone and the like, sympathomimetic drugs such as epinephrine, amphetamine, ephedrine, norepinephrine and the like, cardiovascular drugs, for example, procainamide, amyl nitrate, nitroglycerin, dipyridamole, sodium nitrate, and mannitol nitrate, diuretics, for example, chlorothiazide and flumethiazide, antiparasitic agents such as bephenium hydroxynaphthoate, dichlorophen, enitabas, and dapsone, neoplastic agents such as mechloroethamine, uracil mustard, 5-fluorouracil, 6-thioguanine and procarbazine, hypoglycemic drugs such as insulin, isophane insulin suspension, protamine zinc insulin suspension, globin zinc insulin, extended insulin zinc suspension, and other like insulins derived from animal and synthetic origin, tolbutamide, acetohexamide, tolazamide and chlorpropamide, nutritional agents such as vitamins, essential amino acids, and essential fats, diuretics such as acetazolamide, eye drugs such as pilocarpine base, pilocarpine hydrochloride, pilocarpine nitrate, tetracycline, bacitracin, chlorotetracycline, erythromycin, iodoxuridine, hydrocortisone, eserine, phospholine, iodide, scopolamine, and other beneficial active agents.

The useful agents can also be in various forms, such as uncharged molecules, components of molecular complexes, pharmacologically acceptable salts such as hydrochloride, hydrobromide, sulfate, laurates, palmatates, phosphate, nitrate, borate, acetate, maleate, tartrate, oleates, and salicylates. For acidic drugs, salts of metals, amines or organic cations, for example quaternary ammonium can be employed. Furthermore, simple derivatives of the drug such as esters, ethers, amides and the like which have solubility characteristics that are suitable for the purpose of the invention can also be used herein. Also, a product, agent or drug that is water insoluble can be used in a form that is a water soluble derivative thereof to effectively serve as a solute, and on its release from the device it is converted by enzymes, hydrolyzed by body pH, or other metabolic processes to the original form or to a biologically active form. Additionally, drug or other formulation within the device chamber can have various art known forms such as solution, dispersion, paste, cream, particle, granule, tablet, emulsions, suspensions, powders and the like.

Various osmotically effective solutes including organic and inorganic compounds are advantageously used when it is desired to release a composition, product, agent, drug or the like having limited solubility in the solvent of the environment and now present in the compartment, for example, water from the device. The term "limited solubility" as used herein means that the compound has a solubility of about less than 1% by weight in the internal fluid present in the compartment, that is, the ratio of the weight of the compound in solution to the weight of the water of that solution is less than 1%. The term includes low, slightly and moderate solubility of the composition in the fluid. The osmotically-effective compounds or solutes confined in the device are a substantial motive force of the device and they exhibit an osmotic pressure gradient against an external fluid across the membrane while the membrane is substantially impermeable to the passage of the osmotically-effective solute to prevent loss thereof through the membrane. The solutes are conveniently used by dispensing or homogeneously or heterogeneously mixing a solute or a mixture of solutes with the composition, active agent, product or the like either before they are charged into the compartment or by self mixing after charging a solute and composition into the compartment. In operation, these solutes osmotically attract fluid into the device to produce a solution of the solute which is released from the device concomitantly transporting therewith undissolved and dissolved composition, product, drug or the like. Various osmotically-effective solutes include compounds such as magnesium sulfate, magnesium chloride, sodium chloride, lithium chloride, potassium solfate, sodium carbonate, sodium sulfite lithium sulfate, potassium chloride, salcium bicarbonate, sodium sulfate, calcium sulfate, potassium acid phosphate, calcium lactate, d-mannitol, urea, inositol, magnesium succinate, tartaric acid, soluble carbohydrates such as raffinose, succrose, glucose, $\alpha$-d-lactose monohydrate, mixtures thereof and the like. The solid solute, present initially in excess, can be in any suitable physical form such as particles, crystals, pellets, tablets, strips, film, granules and the like.

In one embodiment for the release of drug having limited insolubility in the entering water, drug particles released from a dissolving drug core are essentially stably suspended in a solution and remain in this phase until released from the device. This embodiment is effected by forming a drug core formulation comprised either of a protective colloid or a dispersant for the drug and an osmotically-active solute that is preferably a non-ionic solute to substantially avoid any drug particle coagulation in solution. A spontaneously dispersed drug can be prepared by predispersing the selected drug in an aqueous solution of, for example, a water-soluble gum such as poly(vinyl pyrrolidone), soluble starch, carboxymethylcellulose, poly(vinyl alcohol), gelatin, and the like, and then spray-drying the mixture to produce a dry powder. Spontaneous dispersibility of the drug can also be achieved by granulating in a coating pan, fluidized bed or the like a mixture of drug and the osmotically-active solute in the presence of a solution of non-toxic surface active agents such as glyceryl monostearate, lecithin, bile acid salts and commercially-available Tween ®, Span ®, Triton ® surfactants, such as sorbitan mono-oleate, polysorbate 80 and the like.

The agent or drug particles in suspension suitably mixed with osmotic solute and preferably optionally mixed with a therapeutically acceptable surfactant is released from the device free of any needed stirring rate dependent force. The drug particles in this suspension are manufactured smaller than the size of the passageway to insure their free passage to the exterior of the device. Generally, any suspension will freely move through the passageway if the maximum particle diameter is from about ¼ to 1/10 or smaller in size than the diameter of the passageway. For example, drug particle relative in dimension to the just-described passageway can be from 50 to 5 microns or less to insure their passage therethrough.

In the novel and useful embodiment just described, drug particles immediately adjacent to the area of dissolving osmotically-active solute are first released from the device. This occurs under osmotic kinetics when particles of drug and solute are in intimate admixture and the rate of drug release from such a device can be computed from the following formula:

$$R_D = \frac{f_D}{1 - f_D} \cdot Q_{OSM} C_O$$

wherein $R_D$ is the drug delivery rate expressed as mg/hr, $f_D$ is the weight fraction of drug in the core, $Q_{OSM}$ is the rate of osmotic uptake of water expressed in ml/hr, and $C_O$ is the saturation concentration of osmotically active solute expressed as mg/ml. The active agent can also be released from the device in a solubilized form of miscelle structure as described in *Physical Pharmacy*, by Martin et al., pages 462 to 465, Second Ed., 1969, published by Lea and Febiger. Additionally, insoluble drug can be mixed with a complexation agent to provide a soluble complex as described in just-mentioned references at pages 325 to 352.

Additionally, the agent or the like and solute can be used in a mixed form by mixing the composition or product with a binder. The product in powdered, granular, pieces and the like form, is homogeneously or heterogeneously dispersed in the binder which binder is water soluble or water insoluble but will release the product on contact with water. Typical water soluble binders include poly(ethylene glycol), gelatin, agar, carboxycellulose, ethylmethylcellulose, poly(vinyl alcohol), poly(vinylpyrrolidone), water soluble starch derivatives and the like. Typical water insoluble binders that can comprise about 1 to 50% of the composition include cellulose acetate, poly(urethane), epoxides and other insoluble binders that permit the free movement of water into the pores of the structure to transport the product from the binder.

The amount of agent present in the device, whether soluble, a derivitized soluble form thereof, is generally non-limited and it is an amount larger than or equal to the amount of agent that is necessary to osmotically operate the device and on its release from the device is effective for bringing about the agent's desired effect. Since the invention contemplates a variety of devices of various sizes and shapes, for a variety of uses, there is no critical upper limit on the amount of agent incorporated in the device. The lower limit will depend on osmotic activity, the span of the release of the product and the activity of the product. Generally, the device will contain about 0.01 to 90% or higher of agent or a mixture of agent and solute based on the weight of the agent or agent solute to the volume of the device, and the like. Typically, the device can be of such size and shape to release 0.01 to 5 cc lesser or higher amounts of agent contained in the fluid per hour, day, month or longer, such as 1 to 10 cc of agent solution for 1 to 10 days, and the like.

The expressions "passageway" and "passageway communicating with" as used herein are comprised of those means and methods suitable for osmotically releasing agent from the device under the osmotic pumping rate of the device. The expression includes an aperture, orifice, bore, porous element through which agent can migrate, hollow cellulose acetate fibers suitable for passing the product, capillary tubes, and the like. The expression also includes bioerodible materials that erode in the environment of use to produce a passageway of precontrolled dimensions. Typical bioerodible materials suitable for forming a passageway include erodible poly(glycolic) and poly(lactic) fibers, erodible gelatinous filaments, poly(vinyl alcohol), and the like.

The rate of release of agent from an uncoated device can easily be determined by those skilled in the art by standard procedures. In this manner, particular materials used for the device wall and the agent or agent solute can be selected for manufacturing the device. Generally, the rate of release of agent from the device is easily ascertained by calculating or measuring the amount of agent, p, released per unit time expressed as $Q_p/t$ wherein $Q_p$ is the quantity of agent released in grams in unit time $t$ hours. The thermodynamic driving force for fluid permeation, that is, the driving energy for attracting the external fluid into the device, is the difference in free energy of the fluid in the two solutions outside and inside the device, which energy can be related to the difference of the fluid concentration and the osmotic pressure. In the devices of the invention, the volume of solution delivered contains a volume of agent or drug inversely proportional to the agent's or drug's density $\rho$ in grams per cc which indicated the desirability of a correction factor in the expression for the volume release rate $V/t$ from the osmotic agent or drug solution released from the device, solubility of agent is defined as the solubility of the agent in grams, g, per cubic centimeter, cc of fluid or S expressed g/cc. The pumping rate of solution $V/t$ from the device is conveniently expressed by combining $Q/t$ and S and $\rho$ to give the equation $$\frac{V}{t} = \frac{Q_p}{t} \times \frac{1}{S} (1 + \frac{S}{\rho})$$

wherein the solution pumping rate in cc/hr, Q, t, $\rho$ and S are as previously set forth. The osmotic volume flow $V/t$ of solution from the device is conveniently expressed as $$\frac{V}{t} = k \frac{A}{h} (\sigma \pi - \Delta P)$$

wherein $A$ is the total exposed area of the membrane of the device, $h$ is the thickness of the membrane, $\sigma$ is the osmotic relection coefficient of the membrane for the membrane for the solute, and as used hereafter by way of example it is assumed to be equal to unity as is valid for ideal situations, $\pi$ is the osmotic pressure of the agent drug solution, $\Delta P$ is the hydrostatic pressure difference between the internal and external pressure and $k$ is the permeability of the membrane as defined immediately below. The permeability of the membrane to an external fluid is described by the known equation $$k = \frac{\text{volume} \times \text{thickness of membrane}}{\text{area} \times \text{time} \times \pi}$$

wherein the thickness of the membrane is expressed in mils, the area in cm², volume is the permeated volume in cc, and $\pi$ is the osmotic pressure approximated by van't Hoff's Law and expressed in the formulae given as follows: $\pi = C \times i \times R \times T$ wherein $C$ is the concentration of the agent in moles per liter, $i$ is the number of ions or particles per molecule of the agent, $R$ is the gas constant and $T$ is the absolute temperature in degrees Kelvin. *Reverse Osmosis Membrane Research*, Edited by Lonsdale and Podall, pages 17 to 42, 1972 published by Plenum Press, New York.

The size of the passageway in the devices of the invention is designed so that the rate of agent delivered, $Q_D/t$, attributed to diffusion in the fluid present in the passageway is always less than the rate of pumping $Q_P/t$ through the passageway. The expression $Q_D$ is the amount of drug expressed in grams diffusing through the passageway in $t$ time, expressed in hours, and $Q_P$ is the amount of agent delivered by pumping in the time $t$ in units of grams/hours. The quantity $Q_P/t$ is determined by the amount of fluid which permeates through the membranes as controlled by the permeability of the membrane and its thickness and the osmotic pressure difference across the membrane. In the devices of the invention, $Q_P/t$ is greater than $Q_D/t$ which assures that the device is essentially as osmotic powered device. By combining the above equations, it is immediately obvious that the product rate of release from the device of the invention is encompassed by the following equation:

$$\frac{Q_P}{t} = k \frac{A_m}{t_m} \times \text{osmotic pressure} \times \frac{\text{drug solubility}}{1 + \frac{\text{drug solubility}}{\text{drug density}}},$$

wherein $A_m$ = area of membrane, $t_m$ = thickness of membrane, and wherein $k$ is the permeability coefficient defined as $$\frac{\text{cc of fluid}}{\text{hr cm}^2} \times \frac{\text{thickness or membrane}}{\text{osmotic pressure}}.$$

The above presentation along with methods for measuring flow rates and the like are described in *Encycl. Polymer Sci. Technol.* Vol. 9, pages 659 to 688, 1968 published by Interscience Publishers, in *Encycl. of Chem. Technol.*, Vol. 14, pages 345 to 356, 1967, published by Interscience Publishers, and in *Desalination by Reverse Osmosis*, Merten, U., pages 15 to 54, 1966, published by the M.I.T. Press, Cambridge, Mass.

The operative size of the passageway in any given osmotic device made according to the mode and manner of the invention can easily be ascertained from the immediate equation wherein the maximum size of the passageway is $$\frac{A_s}{h} = \frac{1}{F} \times \frac{Q_p}{t} \times \frac{1}{DS}$$

wherein $A_s$ is the cross sectional area of the passageway, $h$ is the length of the passageway and for a device with a passageway through a membrane it corresponds to the thickness of the membrane, $D$ is the diffusional coefficient of the active agent in the solution osmotically attracted into the device, $F$ is the ratio of mass of active agent delivered per unit time conveniently stated at $Q_P/t$, to the mass of agent or drug $Q_d/t$ delivered per unit time through the solution in the passageway in the absence of any measurable osmotic pumping so the ratio of $F = Q_{p/t}/Q_{d/t}$ is always at least 2 and preferably greater than 10 and usually in a presently-preferred range of from 10 to 1000, wherein $S$ is as previously defined.

The size of the passageway is constructed with a minimum size so that size thereof is sufficiently large to essentially prevent hydrostatic pressure $\Delta P$ buildup in a device. This minimum size can be determined, for example, for a cylindrical passageway by the following general equation $$A_s = \left[ \frac{LV}{t} \times 8\pi \times \frac{\eta}{\Delta P} \right]^{\frac{1}{2}}$$

wherein $A_s$ is the cross-sectional area of the passageway, $\pi$ is 3.14, $\eta$ is the viscosity of the solution in the passageway leaving the device, $\Delta P$ is hydrostatic pressure difference between the inside and the outside of the device, at which the device osmotically pumps agent without substantially deforming or rupturing the wall of the device and it is preferably less than 20 atmospheres, $L$ is the length of the passageway and $V/t$ is as previously defined.

The novel and useful devices of the invention are made with at least one passageway. The number of passageways for any device is easily ascertained as $A_s \geq N \cdot A_h$ wherein $A_s$ is as previously defined as the total cross sectional area of the passageway and it is equal to or larger than the number of passageways N times the area $A_h$ for N indicated passageways. When the devices of the invention are fabricated with more than one passageway, the number and position of these passageways is determined by following the teachings disclosed therein, for example, by measuring the delivery rate from the device as passageways are added to ascertain that any unusual convection of fluids is not perturbing and altering the usual pattern of agent delivery from the device.

The solubility of an agent in a fluid can be determined by various art known techniques. One method consists in preparing a saturated solution, for example, a fluid plus agent and ascertaining by analysis the amount of agent present in a definite quantity of the fluid. A simple apparatus for this purpose consists of a test tube of medium size fastened upright in a water bath maintained at constant temperature and pressure, for example, 37.5° C and one atmosphere. The fluid and agent are placed in the tub and stirred by means of a motor driven rotating glass spiral. After a given period of stirring, a definite weight of the fluid is analyzed and the stirring continued for an additional period of time. If the analysis shows no increase of dissolved substance after successive periods of stirring, in the presence of excess solid product in the fluid, the solution is saturated and the results are taken as the solubility of the agent in the fluid. Numerous other methods are available for the determination of the solubility of an agent in a fluid. Typical methods used for the measurement of solubility are chemical analysis, measurement of density, refractive index, electrical conductivity, and the like. Details of various methods for determining solubilities are described in *United States Public Health Service Bulletin, No. 67* of the Hygienic Laboratory; *Encyclopedia of Science and Technology*, Vol. 12, pages 542 to 556, 1971, McGraw-Hill, Inc., *Encyclopedia Dictionary of Physics*, Vol. 6, pages 545 to 557, 1962, Pergamon Press, Inc.; and the like.

The term "permeation" or "permeation process" as used herein means the transfer or migration of the external fluid through the wall of the device into the agent compartment. The permeation process generally depends on the thermodynamic activity gradient for the medium across the wall, and the properties of the rate controlling membrane. These latter properties are reflected in the solubility and the diffusity of the fluid through a homogeneous membrane or through a medium in the pores of a heterogeneous membrane. See for example, *Diffusion in Polymers,* by Crank, J. and Park, G. S., Chapter 8, pages 259 to 313, 1968, published by Academic Press, N.Y.

The flux of an external fluid, for example, the rate of water vapor transmission through various wall forming materials is determined by using the procedures of *Diffusion in Polymers,* pages 1 to 39 and then expressing the results as WVTR or water vapor transmission rate through a film in grams/100 in$^2$/24 hr/one mil thick film. Known WVTR values can also be found in *Plastic Film Technology,* Park, W. W. R., 1969, published by Van Nostrand-Reinhold Inc., and in *Diffusion in Polymers,* pages 274 to 276. Typical values are set forth in Table 1 immediately below wherein film is the material and WVTR is as defined.

TABLE 1

| Film | WVTR |
|---|---|
| Polyvinyl alcohol | 100 |
| Polyurethane | 30–150 |
| Methylcellulose | 70 |
| Cellulose acetate | 40–75 |
| Ethylcellulose | 75 |
| Cellulose acetate butyrate | 50 |
| Polyvinylchloride, cast | 10–20 |
| Polyvinylchloride, extruded | 6–15 |
| Polycarbonate | 8 |
| Polyvinylfluoride | 1–3 |
| Polyesters | 2 |
| Cellophane, polyethylene coated | >1.2 |
| Polyvinylidene fluoride | 1.0 |
| Polyethylene | 0.5–1.2 |
| Ethylene propylene copolymer | 0.8 |
| Polypropylene | 0.7 |
| Polyvinyl chloride, rigid | 0.7 |

The coating materials used herein may be coated onto the semi-permeable wall according to their respective properties. For example, the poly(carboxylic acids) coatings employed in the devices of this invention are generally soluble in organic solvents and this feature lends itself to be used as a means for coating same. Accordingly, the polyacids coatings may be conveniently applied by standard film casting techniques. An organic solvented solution of the polyacid is prepared and cast or drawn to a film. The solvent is then evaporated to yield a continuous film of the polyacid.

A wide range of organic solvents may be used for the casting of the coating. With poly(carboxylic acid) materials having total carbon to carboxylic hydrogen ratios at the lower end of the range specified for this invention, such as ratios in the range of from about 8:1 to about 11:1, it is generally preferred to use relatively polar organic solvents, that is, organic solvents having dielectric constants, as listed in the 51st Edition of the Chemical Rubber Company "Handbook of Chemistry and Physics" at pages E-62 through E-64, of greater than about 15, for example; lower alkanols such as methanol, ethanol, the propanols, 1 and 2-butanol; lower alkanones such as acetone, diethyl ketone, ethyl methyl ketone and cyclohexanone and halogenated and nitrogenated solvents such as 2-chloroethanol, and nitrobenzene. With polycarboxylic acids having higher ratio of total carbon atoms to ionizable hydrogens, such as from about 14:1 to 22:1 it is generally preferred to use less polar organic solvents, such as those having dielectric constants of less than about 15, especially less than about 10, for example; ethers such as diethyl ether, isopropyl ether and the like; hydrocarbons such as cyclohexane, benzene and toluene, and other low dielectric materials such as ethyl acetate. With the intermediate ratio poly(carboxylic acids) either group of solvents may be used with the alkanols and alkanones generally being favored. The casting and drying of the poly(carboxylic acids) are carried out at moderate conditions such as at ambient temperature and pressure. Solvent removal may be facilitated by the use of vacuum or slightly elevated temperatures.

It is often desired to incorporate plasticizers in the coatings, for example in the poly(carboxylic acid) coatings, to improve or vary their physical properties. Exemplary plasticizers suitable for use for the present purpose are the pharmaceutically acceptable plasticizers conventionally used, such as acetyl tri-n-butyl citrate, epoxidized soy bean oil, glycerol monoacetate, polyethylene glycol, propylene glycol dilaurate, decanol, dodecanol, 2-ethyl hexanol-2,2-butoxyethoxyethanol and the like. The proportion of optional plasticizer used will vary within broad limits depending upon the characteristics of the poly(carboxylic acid) involved. In general, from about 0.01 parts to about 1.0 parts by weight of plasticizer for each part by weight of the poly(carboxylic acid) can be used. When plasticizers are included in the poly(carboxylic acid) coatings, they are most suitably added prior to coating the final formed structure, such as by dissolving or dispersing them in the solution from which the form is cast.

The release rate profile for the coating is governed by the coating and the environment in which the device is placed for release of agent. Thus, controlled rates of erosion of a coating of a poly(acid) type can occur in environments having a pH throughout the period of use of the device in the range of about 6.0 to about 9.0. In actual application, the osmotic drug delivery devices find use in many environments. For example, these include, in addition to the gastrointestinal tract which presents both acidic and base pH environments, the ocular cavity with a pH of about 7.4, the rectum with a pH of about 7.5, the pH of the uterus at 7.3, or vagina at about 7.3, and the pH of blood which is normally constant at about 7.2. When a device in accord with this invention carrying drug is applied to any of these body areas, or similar body areas, coat 9 erodes at a controlled and constant rate over a prolonged period of time to exposure or let fluid migrate to wall 14. Additionally, the products of this erosion of the coat 9 are innocuously passed from the body. Coatings made of poly(carboxylic acid) have proven especially advantageous for erosion-controlled release rate profile materials. Without intent to limit the scope of this invnetion by theoretical considerations, it is believed that the uniform and controllable rates or erosion observed with the coatings hydrophobic poly(carboxylic acids) having an average of 8 to 22 carbons for each ionizable acidic-carboxylic hydrogen are the result of equilibriums inherent in the erosion of these poly(carboxylic acids). As shown in general formula I, the poly(carboxylic acids) of this invention may be represented as:

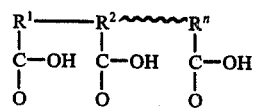

The carboxyl groups are weak acids which, in their unionized form, are hydrophobic. When placed in an aqueous fluid a portion of the carboxyl groups ionized to yield hydrophilic

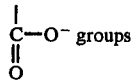

and hydronium ions ($H_3O^+$). As more of the carboxyl groups in an initially hydrophobic polymer chain ionize, the chain assumes an increasingly hydrophilic character and eventually erodes in the fluid. This erosion by ionization occurs on the outer surfaces of the polycarboxylic acid bodies, while continually migrating with the newly formed surface. Even if minor amounts of fluid do penetrate the coating, insignificatn ionization can occur there since the inner carboxyl groups, being surrounded by an essentially organic medium exhibit a far higher pKa than do the carboxyl groups on the surface which are in a more aqueous medium.

The bioerosion by surface ionization for the poly(carboxylic acid) coatings is sensitive to pH. As hydronium ions are generated, they tend to cluster about the coating from which they were generated to inherently somewhat lower the pH in the specific area of the body, which inherently governs further ionization. Some of the clustered hydronium ions gradually disperse or are consumed by the fluid and are replenished by further ionization while exposing more surface. The overall erosion rate which results with the poly(carboxylic acids), as used herein, is therefore suited for use as erodible release rate profile coatings to expose surface over prolonged periods of from about 1 to 2 hours to about 120 days, or longer.

The rate of erosion of coatings used in the invention can be determined experimentally in vitro by testing them under simulated environmental conditions. For example, the rate of erosion of a coating in a moving aqueous stream can be determined by placing a coating on a substrate in such a stream and repeatedly weighing it to determine its weight loss. Similarly, the rate of erosion of a coating in tear fluids, as would occur with an ocular drug delivery device, may be measured by placing a small weighed sample of the material in a 0.026 M $HCO_3^-$ solution of pH about 7.4, which is simulated tear fluids, at body temperature (37° C), agitating for a timed interval, and periodically measuring the amount of coating eroded into the solution. Other procedures will become apparent to those versed in the art from a reading of this disclosure and its accompanying examples.

The novel devices of the invention are fabricated by standard techniques. For example, in one embodiment the agent, or the agent and a binder and/or a solute is mixed or formulated into a solid, semi-solid, or like form by conventional methods, such as ball milling, calendering, stirring, shrinking, roll milling and the like and then charged into the compartment of the device. The wall material forming the device and having the agent contained therein can be formed into a given shaped device, in one embodiment, by molding or casting the one wall, pressing a middle wall thereto, charging the compartment, and then selaing a third wall to form the device. A passageway leading through one wall is fabricated by drilling, punching, casting around a fiber that is removed therefrom, casting around a wire of known diameter that is then removed, cutting, or depositing a tube in one wall during assembly of the device. The device can also be formed of a continuous wall by pouring, casting or the like a wall forming material around a removable mold of any desired shape. The devices when formed of more than one wall can be joined by various joining techniques, such as high frequency electronic sealing that provides clean edges and firmly sealed devices. By using, for example, high frequency sealing, the wall forming materials flow melt at the point of contact to suitably join the walls into a composite article of manufacture. The ability to design and shape the wall into an osmotic device of highly reproducible shapes of controllable composition, readily results in the fabrication of osmotic delivery devices with controlled characteristics and thus overcome a significant disadvantage of previously-described devices. Other standard manufacturing procedures are described in *Modern Plastics Encyclopedia*, Vol. 46, pages 62 to 70, 1969, and these are well-known to those skilled in the art and can be used to fabricate the osmotic delivery devices of the invention.

The devices can be coated with a release rate profile coating by standard means. One suitable method includes the steps of dispersing a coating material in a volatile solvent. To this liquid coating composition may be added dyes and complexing agents. The resulting mixture is applied to the device in a coating pan, by dipping, spraying or the like. The coating composition is distributed over the surface of the device and additional portions of the coating are added as the solvent from the previous portion evaporates. Each of these steps results in a dry film formed on the semi-permeable wall. The procedure is repeated until a coating of the desired thickness is obtained for the device.

The novel and oral osmotic drug delivery devices of the invention can be of any preselected shape and in a presently-preferred embodiment it is of standard tablet configuration. Generally, the tablet is discoid in shape, although it may be oval, oblong, round, cylindrical, triangular and the like. The upper and lower surfaces may be flat, round, concave, convex or the like. The oral osmotic tablet may be manufactured by standard manufacturing methods such as the wet granulation method, drum granulation, compression, slugging and the like. The oral tablet may be coated with a semi-permeable osmotic membrane of varying thickness by pan coating, spray-pan coating, laminating coating techniques, dip coating, Wurster air-suspension coating, and the like. The semi-permeable membrane is then coated with a release rate profile coating in like technique or according to the procedure previously described. The oral device may be glazed, polished, colored and the like to esthetically enhance the oral device. These procedures and similar manufacturing techniques are known to the art in *Remington's Pharmaceutical Science*, Fourteenth Edition, pages 1649 to 1968, 1970, published by Mack Publishing Company, Easton, Penna., and in *The Theory and Practice of Industrial Pharmacy*, by Lachman et al., pages 197 to 225, 1970, published by Lea & Febiger, Philadelphia, Penna.

The following examples are merely illustrative of the present invention and they should not be considered as limiting the scope of the invention in any way, as these examples and other equivalents thereof will become apparent to those versed in the art in the light of the present disclosure, drawings, and the accompanying claims.

EXAMPLE 1

An osmotic ocular drug delivery device for the continued release of pilocarpine nitrate at a release rate of 100 μg/hr from a device with a 1.2 cm² membrane area and 3 mil membrane thickness, with the pilocarpine nitrate having a solubility of 0.250 g/ml in water and the ocular device designed with an eliptical shape is constructed as follows: first, the predetermined pumping rate of an uncoated device for releasing pilocarpine nitrate is calculated from the above presentations as follows 4.10⁻⁴ ml/hr according to the equation $$100 \text{ μg/hr} \times \frac{1}{0.250 \text{ g/ml}}$$

which requires a corresponding water flux through the membrane 3 mil thick and 1.2 cm² of $$\frac{4.10^{-4} \text{ ml} \times 3 \text{ mil}}{\text{hr} \times 1.2 \text{ cm}^2}.$$

The flux can be expressed for pilocarpine nitrate through a 1 cm² area with 1 mil thickness under the osmotic driving force of pilocarpine nitrate as $10^{-3}$ (cc·mil/hr·cm²). The driving force of pilocarpine nitrate for the device is expressed as the osmotic pressure $$\pi = 25 \times 2 \times \frac{250 \text{ g}}{\text{liter} \times 270 \text{ g/mole}}$$

where 2 is the number of ions in a molecule of pilocarpine nitrate and 25 is the product of the gas constant times the absolute temperature of about 300° K. From this experiment was found to be about 50 atmospheres. From an osmotic system comprised of a cellulose acetate wall and the osmotically effective solute potassium sulfate with $\pi$ of 58 atm, the water flux through the cellulose acetate was measured at $10 \times 10^{-3}$ (cc·mil/hr·cm²). The device of this example is constructed with a membrane having a water permeability about 10 times less than cellulose acetate, that is, a semipermeable wall made of polyurethane with the device's orifice having a length of 1 mm and a diameter of 2 mil to produce the desired constant rate of drum release.

A release rate profile coating of a hydrophobic poly(carboxylic acid) polymer having an average of 8 to 22 carbon atoms for each ionizable acidic carboxylic hydrogen was prepared as follows: first, 12.6 grams (0.10 equivalents) of ethylene-maleic anhydride copolymer (Monsanto EMA, Grade 31) is stirred with 50 ml (0.4 moles) of n-hexyl alcohol at 120°-125° C for 7 hours. The solution is cooled to room temperature and methylene chloride is gradually added to the cloud point. Then more methylene chloride is added to precipitate the product (total vol. 3l). The precipitate is thoroughly leached with the methylene chloride. The solvent is decanted and the product dissolved in 75 ml warm acetone. Methylene chloride is added to the cloud point. Then more methylene chloride is added to precipitate the product (total vol. 2l). The precipitate is then thoroughly leached with the methylene chloride. The solvent is decanted and the product dissolved in 75 ml acetone. The solution is transferred to a polypropylene container and solvent is removed under vacuum at 50° C to yield the polymer product. The infrared spectrum of the polymer shows broad bands at 1680 and 1780 cm⁻¹ indicative of ester carboxyl. Titration with base shows that the hexyl half ester of maleic acid has been formed, and thus the ratio of total carbons to ionizable hydrogens on average is 12:1. A sample of the coating is tested for hydrophobicity by measuring its water absorption and is found to pick up only 6% by weight of water.

Next, about 1.8 to 3.7 grams of the coating is dissolved in 10 ml of acetone with constant stirring at 25° C and atmospheric pressure. The resulting semi-viscous dispersion is doctor-blade spread on the semi-permeable membrane and allowed to dry to yield a 0.3 to 0.4 mm coating. This coating bioerodes in simulated tear fluid at a uniform rate to expose semi-permeable wall at the same rate. The device then releases drug as previously described.

EXAMPLE 2

An osmotic drug delivery device is manufactured according to the procedure of Example 1 wherein the conditions were as described except that in Example 2 the device had an orifice length of 3 mils, an orifice area of $16.5 \times 10^{-7}$ cm², an orifice having a radius of $0.73 \times 10^{-3}$ cm, an orifice diameter of 0.6 mil, a pressure difference across the orifice of $8 \times 10^{-5}$ atm, a coating of 0.5 mm and the release rate of 100 μg/hr.

EXAMPLE 3

An osmotic drug delivery device manufactured with an ellipse shape and comprised of two outer semi-permeable walls coated with a release rate pattern bioerodible material and each fused to an inner middle wall having a center area defining a space and which middle wall extends around and interbonds the internal perimeter of the two outer walls to form an osmotic drug delivery device having a drug compartment for containing a drug and a passageway through positioned between the middle and one of the outer walls is manufactured as follows: first, an essentially uniform wall of a semi-permeable material is formed by thoroughly mixing commercially available polyurethane ether, commercially available as Estane ® 5714 from the B. F. Goodrich Co., with tetrahydrofuran in a concentration ratio of 25% of polyurethane to 75% of the solvent and casting the slurry into a silicone release paper substrate. The solvent is allowed to evaporate at room temperature and the film warm-air dried to yield a drug release rate wall material about 2.5 mils thick. Two walls, each about 16 mm × 6.75 mm are pressed from the film for use as the semi-permeable walls of the device. Next, a middle wall is prepared by mixing ethylene vinylacetate, methylene chloride and Food Drug and Cosmetic blue lake in a percent ratio of 20 to 80 to 9.1 and the ingredients thoroughly mixed in a commercial laboratory v-blender. The slurry is then cast onto a silicone release paper substrate, and the solvent evaporated at room temperature. The film is warm air dried to yield a film 4.2 ± 0.3 mils thick. Next, this film is press cut into an ellipse having the same dimensions of the just press cut polyurethane walls. The middle wall is press cut with the center area punched out to yield a continuous ellipse defining an opening. Then, onto one of the semi-permeable walls is placed the middle wall and these two walls placed into a conventional standard vacuum laminator. Next, a vaccum is pulled to 29 inches of mercury and held for 3 minutes. At the end of 3 minutes, a high flux radiant heater is positioned over the walls and heated for about 15 seconds or until the temperature reaches 90° C. At the end of the heating, a pressure head is applied to the two walls and a pressure of 15 lb. applied for 45 seconds to firmly seal the two walls, and the vacuum released.

Next, a drug core compressed of water soluble pilocarpine nitrate dispersed in ethylene vinylacetate is placed into the compartment, and a passageway formed by laying a porous silk suture over the middle ring and the third wall placed in contact with the middle wall. The three walls are then subjected to a vacuum, and heat laminated as just described to produce a composite article of manufacture. Next, the semi-permeable wall is coated with release rate profile coatings as previously prepared except that n-hexanol is replaced with a similar amount of n-butanol, n-pentanol, n-heptanol or n-octanol. The osmotic drug delivery device, when placed into an adult human eye and upon total exposure of the semi-permeable wall, will administer 30 μg/hr of pilocarpine.

EXAMPLE 4

An osmotic drug delivery device for the prolonged, continuous and controlled rate of drug administration is manufactured according to the procedure of Example 3 with the device comprised of two outer walls each having an anular ring bonded thereto and a hollow fiber positioned between the two outer walls. The hollow fiber connects the exterior of the device with the interior compartments containing pilocarpine nitrate. The two walls with their annular rings are sealed at the annular ring interface as in Example 3. At least one of these walls was previously coated with a release rate profile coat.

EXAMPLE 5

An osmotic delivery device for releasing potassium chloride at an osmotically-controlled rate was made as follows: first, 500 mg of commercially-available potassium chloride was compressed by standard compression techniques using a ⅜ inch punch. The compressed mass was then coated with commercially-available cellulose acetate available as E-320 from Eastman Kodak by using the Wurster air suspension technique. A 5% polymer solution in dioxane was used in the Wurster apparatus to produce the coating which had a final thickness of about 10 mils. A number of drug delivery devices were made using this procedure and a passageway was placed in each device, that is, a passageway through the semipermeable membrane either by mechanical drilling or electric drilling techniques. The diameter of the passageway ranged from 3.9 to 11.0 mils. The osmotic device in the uncoated state had a constant zero order rate of release of 26 mg per hour with a variation of about ±5%. The average results for this just described device is shown in FIG. 13. Next, the semipermeable membrane is coated with an enteric coating that resists the acidity of the stomach to prevent any fluid entering the compartment and release of drug from the device. Useful enteric layers that can be applied include keratin, calcium alginate, shellac and the like. The release profile for this device is first a non-release state in the stomach with a release state in the intestine after disintegration of the coating as illustrated in FIG. 16. Similar osmotic devices can also be made wherein the diameter of the passageway ranges from 0.1 mils or less to 20 mils or higher for each device with at least one passageway in the device, consistent with the other teachings of this specification as set forth herein.

EXAMPLE 6

A non-stirring rate dependent osmotic device that releases agent independent of pH of the environment was prepared as follows: first, 700 mg of sodium phenobarbital was compressed into capsule-shaped cores and then dipped coated in a bath of cellulose acetate E-376 commercially-available from Eastman Kodak. The cellulose acetate was mixed in dioxane solution and the final semi-permeable coating applied to the barbiturate was about 12 mils thick. The devices are free of release rate profile material for comparing these devices with devices coated with release rate profile material. The devices were made with a small wire that was removed after the devices were dried to give a passageway having a 0.4 mm diameter. The osmotic release rate for this device was measured in simulated gastric juice and simulated intestinal juice made without enzyme as described in *The United States Pharmacopeia*, Eighteenth Revision, pages 1026 and 1027, 1970. The results as shown in FIG. 14 demonstrated drug release independent of pH and free of any stirring rate dependency.

EXAMPLE 7

Devices made according to Examples 5 and 6 were orally administered to dogs to demonstrate the osmotic dynamics and the release rate measured over a prolonged period of time. The devices were first weighed and color coded. A series of either devices was administered to two dogs at regular time intervals. After 12 hours, the dogs were sacrificed, the devices uncovered, rinsed, dried and re-weighed. The amount of drug released from each device as determined by weight difference is plotted in FIG. 15 wherein the X and squares represent the dogs. For these devices, the average rate of drug release ascertained from the slope of the line was calculated as 24.3 mg/hr which exhibits the beneficial results obtained for the device of this invention.

EXAMPLE 8

Following the procedure of the above examples an oral, osmotic, unit dosage drug dispensing device was manufactured according to the previously described techniques. When the device containing drug was placed in an aqueous environment, water slowly dissolved the outer coating and then permeated through the semi-permeable membrane and dissolved drug in the compartment to the point of saturation. The water uptake of the device was constant and proportional to the osmotic pressure of the saturated drug solution in the compartment as controlled by the uncoated semi-permeable membrane. As more water entered the compartment it became saturated with drug and the device showed a thermodynamic steady state, zero order rate of drug release resulted. The steady state was maintained throughout the presence of the excess drug in the compartment; which state continually produced the saturated drug solution. Finally, when all the excess drug is released from the device, rate of release from the device gradually declined until the remaining drug is released therefrom.

EXAMPLE 9

The volume delivery rate for an osmotic delivery device made according to the invention is given by $$\left(\frac{V}{t}\right)_1 = \left(\frac{M}{t}\right)_1 \times \frac{1}{S}\left(1 + \frac{S}{\rho}\right)$$

for a semi-permeable membrane with a permeability given by $$\left(\frac{V}{t}\right)_1 = k_1 \pi \frac{A}{h_1}$$

where the permeability is $k_1$, $\rho$ is the drug density in g/cc, $S$ is the solubility of the drug in the fluid in the device, $\pi$ is the osmotic pressure of the drug, A is the membrane area of the device, and $h_1$ is the semi-permeable membrane thickness. The ratio of the fluid permeability of the erodible coating $k_2$ to the erodible coating thickness $h_2$ is as follows: $k_1/h_1 \geqq k_2/h_2$ which makes the erodible coating essentially impermeable to the fluid of the environment so that essentially no pumping of agent occurs until the outside coating is eroded. An osmotic drug delivery device completely coated with such an enteric coating will have a delayed action with the onset of drug delivery completely delayed until the external enteric coating is eroded past the stomach. The delivery release rate profile for a fully enteric coated osmotic device containing 500 mg of potassium chloride is seen in FIG. 16. The device is made with cellulose acetate E-320 semi-permeable membrane and the sole delivery passageway had a diameter of 8.3 mils. *The Theory and Practice of Industrial Pharmacy*, by Lachman, L., et al., pages 209 to 220, 1970, published by Lea and Fiebiger, Philadelphia, Penna.; and *Biopharmaceutics and Relevant Pharmacokinetics*, by Wagner, J. G., First Edition, Chapter 23, pages 158 to 165, 1971, published by Drug Intelligence Publications, Hamilton, Ill.

EXAMPLE 10

An osmotic drug delivery device coated on one side with a drug release rate profile enteric coating that resists gastric juice, pH about 2, and capable of disintegrating in intestinal juice, pH about 7, is manufactured according to the procedure set forth in the previous examples. This device, during its residence time in the stomach will have a release rate of $R_s = F \cdot R$ where R is the release rate of an uncoated device M/t and F is the fraction of the total membrane area which is uncoated. For example a 50% enteric coated device where F is equal to 0.5, formed of several coats of shellac-n-butyl stearate-coated from an absolute alcohol acetone one to one ratio is dried to a smooth surface and it will have the release rate profile as seen in FIG. 17, wherein the initial rate $R_s$ is equal to 0.5 times R. On disintegration of the coating in the alkaline pH, there is a second release rate profile for the device. The device had a semipermeable membrane coated of cellulose acetate, that compartment contained 500 mg of potassium chloride and the passageway had an orifice of 8.3 mils. The device had a zero order rate of release within each drum release rate profile.

EXAMPLE 11

An osmotic drug delivery device shaped like a cylinder and coated with a release rate profile coating that has a constant erosion rate at preselected pH is prepared according to the specification and is illustrated in FIG. 9. The coating on the semi-permeable wall is increased from the passageway to the distant end of the device. The release rate profile materials continually erode at a rate in the range from 10 micron per hour to 1000 micron per hour while simultaneously exposing semipermeable membrane surface. A specific device of cylindrical shape in which the coat is applied under an angle $\theta$, that is the angle between the outside of the semi-permeable wall and the outside coated plane, with the length of the cylinder $l_c$ and a final thickness of $d$ will have an initial drug delivery rate $$\left(\frac{M}{t_o}\right) = k\pi \frac{S}{1+\frac{S}{\rho}} \cdot \frac{A_o}{h}.$$

All the symbols have their previously described meaning and $A_o$ is the initial exposed surface area of the device. The increase in rate is given by $$\frac{d\left(\frac{M}{t}\right)}{dt} = k\pi \frac{S}{\left(1+\frac{S}{\rho}\right)} \frac{1}{h} \frac{dA}{dt}$$

in which $$\frac{dA}{dt} = \pi r^2 \frac{dl}{dt}$$

wherein $r$ is the radius of the cylindrical device, $$\frac{dl}{dt} = \frac{dx}{\sin\theta \, dt}$$

and $dx/dt$ is the erosion rate of the coating as set forth above. The increase in rate per unit time is given by $$\frac{d\left(\frac{M}{t}\right)}{dt} = \frac{1}{l_c}\left(\frac{M}{t}\right) \text{cylinder} \frac{1}{\sin\theta} \frac{dx}{dt}$$

where (M/t) cylinder is the rate from the device contributed by the totally uncoated cylindrical area of the device which for a linear increase in rate is also given by $$\frac{d\left(\frac{M}{t}\right)}{dt} = \frac{\left(\frac{M}{t}\right)_c}{t_t}$$

where $t_t$ is the total time necessary for erosion of all the coating material. A device with an initial rate $(M/t) = 5$ mg/hr and a total rate from the total uncoated cylinder as previously described of $(M/t) = 20$ mg/hr, with the device having a lifetime of $t_t = 10$ hr and the erosion rate of the coating $dx/dt = 100\mu$/hour, and a final coating thickness where $d$ is equal to 1000 $\mu$ will give an increasing result of release as seen in FIG. 18.

The novel, osmotic product delivery device of this invention employs a unique means which facilitates the attainment of precisely-conducted product release rates in the environment of use. While there has been described and pointed out the fundamental novel features of the invention as applied to the presently preferred embodiments, those skilled in the art will appreciate that various modifications, changes and omissions in the osmotic product delivery devices illustrated and described can be made without departing from the spirit of the invention.

We claim:

1. A method for orally administering an active agent at a controlled rate to the gastrointestinal tract of a warm blooded animal comprising,
   A. admitting into the gastrointestinal tract a device comprising;
      (1) a shaped wall formed of a semipermeable material that is permeable to the passage of gastrointestinal fluid and substantially impermeable to active agent, said wall surrounding and forming;

(2) a compartment containing the active agent that is soluble in fluid that enters the compartment and which agent exhibits an osmotic pressure gradient across the wall against the gastrointestinal fluid;

(3) a layer formed of an erodible enteric material on the exterior surface of the semi-premeable wall;

(4) a passageway in the wall for releasing said agent from said device, said passageway having a maximum cross-sectional area $A_s$, of $$\frac{L}{F} \times \frac{Q_p}{t} \times \frac{1}{DS}$$

wherein $L$ is the length of passageway, $Q_p/t$ is the mass of agent released per unit time, $D$ is the diffusion coefficient of agent in the released solution, $S$ is the solubility of agent in the fluid and $F$ has a value of approximately 2 to 1000, said passageway having a minimum area, $A_s$ defined by $$\left[\frac{Lv}{t} \times 8 \times \frac{\pi \eta}{\Delta P}\right]^{\frac{1}{2}}$$

wherein $L$ is the length of the passageway, $t$ is the volume of agent released per unit time, $\pi$ is 3.14, $\eta$ is the viscosity of the solution being released, and $\Delta P$ is the hydrostatic pressure differences between the inside and the outside of the compartment and having a value of up to about 20 atmospheres;

B. bioeroding the enteric layer in the gastro-intestinal fluids in the environment of use at a controlled rate to regulate the amount of fluid available to the wall for imbibition, with fluid imbibed through the wall into the compartment in a tendency towards osmotic equilibrium at a rate determined by the permeability of the wall and the osmotic pressure gradient across the wall thereby continuously dissolving said active agent and, thereby C. dispensing said active agent from the device to the gastro-intestinal tract through the passageway at a controlled rate over a prolonged period of time.

* * * * *